United States Patent
Yan et al.

(10) Patent No.: US 6,630,337 B2
(45) Date of Patent: Oct. 7, 2003

(54) ISOLATED HUMAN KINASE PROTEINS, NUCLEIC ACID MOLECULES ENCODING HUMAN KINASE PROTEINS, AND USES THEREOF

(75) Inventors: Chunhua Yan, Boyds, MD (US); Jane Ye, Boyds, MD (US); Karen A. Ketchum, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 150 days.

(21) Appl. No.: 10/109,854

(22) Filed: Apr. 1, 2002

(65) Prior Publication Data

US 2002/0119548 A1 Aug. 29, 2002

Related U.S. Application Data

(62) Division of application No. 09/810,671, filed on Mar. 19, 2001, now Pat. No. 6,455,291.
(60) Provisional application No. 60/227,470, filed on Aug. 24, 2000.

(51) Int. Cl.[7] ............................. C12N 9/12; C12N 1/20; C12N 15/00; C12N 5/00; C07K 1/00
(52) U.S. Cl. ................. 435/194; 435/252.3; 435/320.1; 435/325; 530/350; 536/23.2
(58) Field of Search ............................. 435/194, 252.3, 435/325, 320.1; 536/23.2

(56) References Cited

U.S. PATENT DOCUMENTS 5,962,232 A 10/1999 Bandman et al. ............... 435/6

FOREIGN PATENT DOCUMENTS

WO WO 00/73469 A 12/2000

OTHER PUBLICATIONS

Schultz, J. et al. "Molecular characterization of a cDNA encoding functional human CLK4 kinase and localization on chromosome 4q35." Genomics vol. 71 pp. 368–370, 2001.
Database EMBL 'Online! Database Accession No. AF294429 Sep. 5, 2000.
Database EMBL 'Online! Database Accession No. AX056410 Jan. 13, 2001.
Database EMBL 'Online! Database Accession No. AR077239 Sep. 12, 2000.
Database EMBL 'Online! Database Accession No. Q9HAZ1 Mar. 16, 2001.
Database EMBL 'Online! Database Accession No. AF033566 Nov. 30, 1997.
Database EMBL 'Online! Database Accession No. AC022182 Jan. 27, 2000.
Database EMBL 'Online! Database Accession No. P49759 Oct. 1, 1996.
Database EMBL 'Online! Database Accession No. O35493 Dec. 15, 1998.
Database EMBL 'Online! Database Accession No. AC022096 Jan. 27, 2000.

*Primary Examiner*—M. Monshipouri
(74) *Attorney, Agent, or Firm*—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

8 Claims, 16 Drawing Sheets

```
   1 GCCAGCTGGG GTTACTTTAA AAAACATGCT CCATGTGCAT CCCTCTTGAA
  51 GCTTCGCACT CTGTTGAAGA GGACACTCAT CCCAGTCATT ATTTAGAAGC
 101 AAGGTCCTTG AATGAGCGAG ATTATCGGGA CCGGAGATAC GTTGACGAAT
 151 ACAGGAATGA CTACTGTGAA GGATATGTTC CTAGACATTA TCACAGAGAC
 201 ATTGAAAGCG GGTATCGAAT CCACTGCAGT AAATCTTCAG TCCGCAGCAG
 251 GAGAAGCAGT CCTAAAAGGA AGCGCAATAG ACACTGTTCA AGTCATCAGT
 301 CACGTTCGAA GAGCCACCGA AGGAAAAGAT CCAGGAGTAT AGAGGATGAT
 351 GAGGAGGGTC ACCTGATCTG TCAAAGTGGA GACGTTCTAA GAGCAAGATA
 401 TGAAATCGTG GACACTTTGG GTGAAGGAGC CTTTGGCAAA GTTGTAGAGT
 451 GCATTGATCA TGGCATGGAT GGCATGCATG TAGCAGTGAA AATCGTAAAA
 501 AATGTAGGCC GTTACCGTGA AGCAGCTCGT TCAGAAATCC AAGTATTAGA
 551 GCACTTAAAT AGTACTGATC CCAATAGTGT CTTCCGATGT GTCCAGATGC
 601 TAGAATGGTT TGATCATCAT GGTCATGTTT GTATTGTGTT TGAACTACTG
 651 GGACTTAGTA CTTACGATTT CATTAAAGAA AACAGCTTTC TGCCATTTCA
 701 AATTGACCAC ATCAGGCAGA TGGCGTATCA GATCTGCCAG TCAATAAATT
 751 TTTTACATCA TAATAAATTA ACCCATACAG ATCTGAAGCC TGAAAATATT
 801 TTGTTTGTGA AGTCTGACTA TGTAGTCAAA TATAATTCTA AAATGAAACG
 851 TGATGAACGC ACACTGAAAA ACACAGATAT CAAAGTTGTT GACTTTGGAA
 901 GTGCAACGTA TGATGATGAA CATCACAGTA CTTTGGTGTC TACCCGGCAC
 951 TACAGAGCTC CCGAGGTCAT TTTGGCTTTA GGTTGGTCTC AGCCTTGTGA
1001 TGTTTGGAGC ATAGGTTGCA TTCTTATTGA ATATTACCTT GGTTTCACAG
1051 TCTTTCAGAC TCATGATAGT AAAGAGCACC TGGCAATGAT GGAACGAATA
1101 TTAGGACCCA TACCACAACA CATGATTCAG AAAACAAGAA AACGCAAGTA
1151 TTTTCACCAT AACCAGCTAG ATTGGGATGA ACACAGTTCT GCTGGTAGAT
1201 ATGTTAGGAG ACGCTGCAAA CCGTTGAAGG AATTTATGCT TTGTCATGAT
1251 GAAGAACATG AGAAACTGTT TGACCTGGTT CGAAGAATGT TAGAATATGA
1301 TCCAACTCAA AGAATTACCT TGGATGAAGC ATTGCAGCAT CCTTTCTTTG
1351 ACTTATTAAA AAAGAAATGA AATGGGAATC AGTGGTCTTA CTATATACTT
1401 CTCTAGAAGA GATTACTTAA GACTGTGTCA GTCAACTAAA CATTCTAATA
1451 TTTTTTGTAAA CATTAAATTA TTTTGTACAG TTAAGTGTAA ATATTGTATG
1501 TTTTGTATCA ATAGCATAAT TAACTTGTTA AGCAAGTATG GTCTTGATAA
1551 TGCATTAGAA AAATTAAAAT TAATTTTTCT TTTTGAAATT ACCATTTTA
1601 AATACCTTTG AAATATCCTT TGTGTCCAGT GATAAATGTG ATTGATCTTG
1651 CCTTTTGTAC ATGGAGGTCA CCTCTGAAGT GATTTTTTTT GAGTAAAAGG
1701 AAATCTTGAC TACTTTATAT TCTTAAAGGA ATATTCTTTA TATACTTCAA
1751 ATTTAGAACT TAACTTTAAA AGTTTTTCTT CTGTAATTGT TGAACGGGTG
1801 ATTATTATTA ACTCTAGATA AGCAGGTACT AGAAACCAAA ACTCAGAAAA
1851 TGTTTACTGT TAGAATTCTA TTAAATTTTA AGTGTTGTAT TCTTTTTCAT
1901 TGGGTGATGT CAGGGTGATA ACCAGACATT CATGGAAAGG CATGCAGTTT
1951 GTCCATTGTG ACAGTTTGTT TAATAAAACC ACATACACAC TTTATTTAAG
2001 ATTAAAATCT AACTGGAAAG TCAGCTTGGA AAATGGACAT TTCCAAGTAT
2051 GTTTGGTGAG TCACAGATAT AAAAATAGAA ATTCTGATGA GAGGTTTCAG
2101 TTTTTAATAC CAAGTCCTTA GGAGTCTTAA CATTGGCCAG CATCTGTTTA
2151 TCAAATGACA TAAATACGTA AACCTATAAG AATTAAGTTT ATTAATTAGG
2201 CAATTTATGT CTGTGATAAT TCTTACGGGA GAAAGAGGAT TTGATTGGAA
2251 AGCAGTTTGG GAAGAAAGTG CTGCTGAAAT TTCCAGAATT TAATTGATTG
2301 GTTACATAAA CTTTTTGACT TCAGAAAAAA AAAATAAAAA AACAAAAAAA
2351 AAAC
(SEQ ID NO: 1)

FEATURES:
5'UTR:       1 - 32
Start Codon: 33
Stop Codon:  1368
3'UTR:       1371
```

FIGURE 1A

Homologous proteins:
Top 10 blast hits:

| Sequences producing significant alignments: | Score (bits) | E Value |
|---|---|---|
| CRA\|150000079514205 /altid=gi\|10190706 /def=ref\|NP_065717.1\| pr... | 904 | 0.0 |
| CRA\|18000005115066 /altid=gi\|6671766 /def=ref\|NP_031740.1\| CDC ... | 883 | 0.0 |
| CRA\|335001098680506 /altid=gi\|11416272 /def=ref\|XP_003664.1\| si... | 745 | 0.0 |
| CRA\|335001098687191 /altid=gi\|11429914 /def=ref\|XP_002520.1\| CD... | 740 | 0.0 |
| CRA\|18000004973971 /altid=gi\|4758008 /def=ref\|NP_004062.1\| CDC-... | 738 | 0.0 |
| CRA\|18000004935844 /altid=gi\|110864 /def=pir\|\|A39676 protein ki... | 718 | 0.0 |
| CRA\|18000004938713 /altid=gi\|125290 /def=sp\|P22518\|CLK1_MOUSE P... | 716 | 0.0 |
| CRA\|114000015334919 /altid=gi\|9437515 /def=gb\|AAF87326.1\|AF2122... | 700 | 0.0 |
| CRA\|18000004896888 /altid=gi\|107458 /def=pir\|\|A38643 protein ki... | 670 | 0.0 |
| CRA\|98000043608390 /altid=gi\|12805489 /def=gb\|AAH02220.1\|AAH022... | 630 | e-179 |

EST:

| Sequences producing significant alignments: | Score (bits) | E Value |
|---|---|---|
| gi\|12603368 /dataset=dbest /taxon=96... | 785 | 0.0 |
| gi\|2555404 /dataset=dbest /taxon=9606 ... | 712 | 0.0 |
| gi\|10341364 /dataset=dbest /taxon=960... | 549 | e-154 |
| gi\|3733981 /dataset=dbest /taxon=9606 ... | 450 | e-124 |
| gi\|900131 /dataset=dbest /taxon=9606 /... | 432 | e-118 |
| gi\|6034370 /dataset=dbest /taxon=9606 ... | 424 | e-116 |
| gi\|2824947 /dataset=dbest /taxon=9606 ... | 396 | e-108 |
| gi\|7318123 /dataset=dbest /taxon=9606... | 381 | e-103 |
| gi\|10913732 /dataset=dbest /taxon=96... | 335 | 2e-89 |

EXPRESSION INFORMATION FOR MODULATORY USE:
library source:
gi\|12603368  Bone osteosarcoma cell line
gi\|2555404   Breast
gi\|10341364  Uterus leiomyosarcoma
gi\|3733981   Fetal heart
gi\|900131    Infant brain
gi\|6034370   Colon-juvenile granulose tumor
gi\|2824947   Mixed
gi\|7318123   Colon-moderately differentiatd adenocarcinoma
gi\|10913732  Bone marrow hematopoietic stem cells
gi: 2824947   Pooled human melanocyte, fetal heart, and pregnant uterus
gi: 10088906  nervous_normal
gi: 9093801 leukopheresis  myeloid cell Tissue expression:
Leukocyte

FIGURE 1B

```
  1 MCIPLEASHS VEEDTHPSHY LEARSLNERD YRDRRYVDEY RNDYCEGYVP
 51 RHYHRDIESG YRIHCSKSSV RSRRSSPKRK RNRHCSSHQS RSKSHRRKRS
101 RSIEDDEEGH LICQSGDVLR ARYEIVDTLG EGAFGKVVEC IDHGMDGMHV
151 AVKIVKNVGR YREAARSEIQ VLEHLNSTDP NSVFRCVQML EWFDHHGHVC
201 IVFELLGLST YDFIKENSFL PFQIDHIRQM AYQICQSINF LHHNKLTHTD
251 LKPENILFVK SDYVVKYNSK MKRDERTLKN TDIKVVDFGS ATYDDEHHST
301 LVSTRHYRAP EVILALGWSQ PCDVWSIGCI LIEYYLGFTV FQTHDSKEHL
351 AMMERILGPI PQHMIQKTRK RKYFHHNQLD WDEHSSAGRY VRRRCKPLKE
401 FMLCHDEEHE KLFDLVRRML EYDPTQRITL DEALQHPFFD LLKKK
    (SEQ ID NO: 2)
```

FEATURES:
Functional domains and key regions:
[1] PDOC00001 PS00001 ASN_GLYCOSYLATION
N-glycosylation site 176-179 NSTD

---

[2] PDOC00004 PS00004 CAMP_PHOSPHO_SITE
cAMP- and cGMP-dependent protein kinase phosphorylation site Number of matches: 2
    1     73-76 RRSS
    2     97-100 RKRS

---

[3] PDOC00005 PS00005 PKC_PHOSPHO_SITE
Protein kinase C phosphorylation site

Number of matches: 8
    1     69-71 SVR
    2     72-74 SRR
    3     76-78 SPK
    4     94-96 SHR
    5   277-279 TLK
    6   303-305 STR
    7   368-370 TRK
    8   425-427 TQR

---

[4] PDOC00006 PS00006 CK2_PHOSPHO_SITE
Casein kinase II phosphorylation site

Number of matches: 8
    1     10-13 SVEE
    2     25-28 SLNE
    3   102-105 SIED
    4   128-131 TLGE
    5   209-212 STYD
    6   247-250 THTD
    7   292-295 TYDD
    8   429-432 TLDE

---

[5] PDOC00007 PS00007 TYR_PHOSPHO_SITE
Tyrosine kinase phosphorylation site

Number of matches: 3
    1    24-31 RSLNERDY
    2    29-36 RDYRDRRY
    3    55-61 RDIESGY

---

[6] PDOC00008 PS00008 MYRISTYL
N-myristoylation site 147-152 GMHVAV

---

FIGURE 2A

[7] PDOC00100 PS00107 PROTEIN_KINASE_ATP
Protein kinases ATP-binding region signature 129-153 LGEGAFGKVVECIDHGMDGMHVAVK
--------------------------------------------------------------------
[8] PDOC00100 PS00108 PROTEIN_KINASE_ST
Serine/Threonine protein kinases active-site signature 246-258 LTHTDLKPENILF Membrane spanning structure and domains:
  ndidate membrane-spanning segments:
  Helix Begin  End  Score  Certainity
    1   324   344   1.141  Certain BLAST Alignment to Top Hit:
>CRA|150000079514205 /altid=gi|10190706 /def=ref|NP_065717.1| protein
    serine threonine kinase Clk4 [Homo sapiens] /org=Homo
    sapiens /taxon=9606 /dataset=nraa /length=481
    Length = 481

Score =  904 bits (2312), Expect = 0.0
Identities = 427/427 (100%), Positives = 427/427 (100%)
Frame = +3

```
Query:   87   HYLEARSLNERDYRDRRYVDEYRNDYCEGYVPRHYHRDIESGYRIHCSKSSVRSRRSSPK  266
              HYLEARSLNERDYRDRRYVDEYRNDYCEGYVPRHYHRDIESGYRIHCSKSSVRSRRSSPK
Sbjct:   55   HYLEARSLNERDYRDRRYVDEYRNDYCEGYVPRHYHRDIESGYRIHCSKSSVRSRRSSPK  114

Query:  267   RKRNRHCSSHQSRSKSHRRKRSRSIEDDEEGHLICQSGDVLRARYEIVDTLGEGAFGKVV  446
              RKRNRHCSSHQSRSKSHRRKRSRSIEDDEEGHLICQSGDVLRARYEIVDTLGEGAFGKVV
Sbjct:  115   RKRNRHCSSHQSRSKSHRRKRSRSIEDDEEGHLICQSGDVLRARYEIVDTLGEGAFGKVV  174

Query:  447   ECIDHGMDGMHVAVKIVKNVGRYREAARSEIQVLEHLNSTDPNSVFRCVQMLEWFDHHGH  626
              ECIDHGMDGMHVAVKIVKNVGRYREAARSEIQVLEHLNSTDPNSVFRCVQMLEWFDHHGH
Sbjct:  175   ECIDHGMDGMHVAVKIVKNVGRYREAARSEIQVLEHLNSTDPNSVFRCVQMLEWFDHHGH  234

Query:  627   VCIVFELLGLSTYDFIKENSFLPFQIDHIRQMAYQICQSINFLHHNKLTHTDLKPENILF  806
              VCIVFELLGLSTYDFIKENSFLPFQIDHIRQMAYQICQSINFLHHNKLTHTDLKPENILF
Sbjct:  235   VCIVFELLGLSTYDFIKENSFLPFQIDHIRQMAYQICQSINFLHHNKLTHTDLKPENILF  294

Query:  807   VKSDYVVKYNSKMKRDERTLKNTDIKVVDFGSATYDDEHHSTLVSTRHYRAPEVILALGW  986
              VKSDYVVKYNSKMKRDERTLKNTDIKVVDFGSATYDDEHHSTLVSTRHYRAPEVILALGW
Sbjct:  295   VKSDYVVKYNSKMKRDERTLKNTDIKVVDFGSATYDDEHHSTLVSTRHYRAPEVILALGW  354

Query:  987   SQPCDVWSIGCILIEYYLGFTVFQTHDSKEHLAMMERILGPIPQHMIQKTRKRKYFHHNQ  1166
              SQPCDVWSIGCILIEYYLGFTVFQTHDSKEHLAMMERILGPIPQHMIQKTRKRKYFHHNQ
Sbjct:  355   SQPCDVWSIGCILIEYYLGFTVFQTHDSKEHLAMMERILGPIPQHMIQKTRKRKYFHHNQ  414

Query: 1167   LDWDEHSSAGRYVRRRCKPLKEFMLCHDEEHEKLFDLVRRMLEYDPTQRITLDEALQHPF  1346
              LDWDEHSSAGRYVRRRCKPLKEFMLCHDEEHEKLFDLVRRMLEYDPTQRITLDEALQHPF
Sbjct:  415   LDWDEHSSAGRYVRRRCKPLKEFMLCHDEEHEKLFDLVRRMLEYDPTQRITLDEALQHPF  474

Query: 1347   FDLLKKK  1367
              FDLLKKK
Sbjct:  475   FDLLKKK  481 (SEQ ID NO:4)
```

FIGURE 2B

>CRA|18000004973971 /altid=gi|4758008 /def=ref|NP_004062.1| CDC-like
    kinase1; CDC-like kinase 1 [Homo sapiens] /org=Homo
    sapiens /taxon=9606 /dataset=nraa /length=484
        Length = 484

Score = 738 bits (1884), Expect = 0.0
  Identities = 352/429 (82%), Positives = 382/429 (88%), Gaps = 2/429 (0%)
  Frame = +3

Query: 84    SHYLEARSLNERDYRDRRYVDEYRNDYCEGYVPRHYHRDIESGYRIHCSKSSVRSRRSSP 263
             SHYLE+RS+NE+DY   RRY+DEYRNDY +G  P H   RD ES Y+ H SKSS RS RSS
Sbjct: 54    SHYLESRSINEKDYHSRRYIDEYRNDYTQGCEPGHRQRDHESRYQNHSSKSSGRSGRSSY 113

Query: 264   KRK-RNRHCSSHQ-SRSKSHRRKRSRSIEDDEEGHLICQSGDVLRARYEIVDTLGEGAFG 437
             K K  R   H +SH+  S  KSHRRKR+RS+EDDEEGHLICQSGDVL ARYEIVDTLGEGAFG
Sbjct: 114   KSKHRIHHSTSHRRSHGKSHRRKRTRSVEDDEEGHLICQSGDVLSARYEIVDTLGEGAFG 173

Query: 438   KVVECIDHGMDGMHVAVKIVKNVGRYREAARSEIQVLEHLNSTDPNSVFRCVQMLEWFDH 617
             KVVECIDH   G HVAVKIVKNV RY EAARSEIQVLEHLN+TDPNS FRCVQMLEWF+H
Sbjct: 174   KVVECIDHKAGGRHVAVKIVKNVDRYCEAARSEIQVLEHLNTTDPNSTFRCVQMLEWFEH 233

Query: 618   HGHVCIVFELLGLSTYDFIKENSFLPFQIDHIRQMAYQICQSINFLHHNKLTHTDLKPEN 797
             HGH+CIVFELLGLSTYDFIKEN FLPF++DHIR+MAYQIC+S+NFLH NKLTHTDLKPEN
Sbjct: 234   HGHICIVFELLGLSTYDFIKENGFLPFRLDHIRKMAYQICKSVNFLHSNKLTHTDLKPEN 293

Query: 798   ILFVKSDYVVKYNSKMKRDERTLKNTDIKVVDFGSATYDDEHHSTLVSTRHYRAPEVILA 977
             ILFV+SDY   YN K+KRDERTL N DIKVVDFGSATYDDEHHSTLVSTRHYRAPEVILA
Sbjct: 294   ILFVQSDYTEAYNPKIKRDERTLINPDIKVVDFGSATYDDEHHSTLVSTRHYRAPEVILA 353

Query: 978   LGWSQPCDVWSIGCILIEYYLGFTVFQTHDSKEHLAMMERILGPIPQHMIQKTRKRKYFH 1157
             LGWSQPCDVWSIGCILIEYYLGFTVF THDSKEHLAMMERILGP+P+HMIQKTRKRKYFH
Sbjct: 354   LGWSQPCDVWSIGCILIEYYLGFTVFPTHDSKEHLAMMERILGPLPKHMIQKTRKRKYFH 413

Query: 1158  HNQLDWDEHSSAGRYVRRRCKPLKEFMLCHDEEHEKLFDLVRRMLEYDPTQRITLDEALQ 1337
             H++LDWDEHSSAGRYV R CKPLKEFML  D EHE+LFDL+++MLEYDP +RITL EAL+
Sbjct: 414   HDRLDWDEHSSAGRYVSRACKPLKEFMLSQDVEHERLFDLIQKMLEYDPAKRITLREALK 473

Query: 1338  HPFFDLLKK 1364
             HPFFDLLKK
Sbjct: 474   HPFFDLLKK 482 (SEQ ID NO:5)

Hmmer search results (Pfam):
Scores for sequence family classification (score includes all domains):
Model       Description                                Score    E-value   N
---------   -----------                                -----    -------   ---
PF00069     Eukaryotic protein kinase domain           272.4    5.9e-78   1
CE00022     CE00022 MAGUK_subfamily_d                   26.7    8.6e-08   2
CE00204     CE00204 FIBROBLAST_GROWTH_RECEPTOR           3.4       2.3    1
PF00548     3C cysteine protease (picornain 3C)          1.6       7.7    1
CE00031     CE00031 VEGFR                                0.7       2.5    1
CE00289     CE00289 PTK_PDGF_receptor                  -49.9    0.0045    1
CE00292     CE00292 PTK_membrane_span                 -102.3    0.0063    1
CE00287     CE00287 PTK_Eph_orphan_receptor           -117.7      0.97    1
CE00291     CE00291 PTK_fgf_receptor                  -138.4      0.73    1
CE00290     CE00290 PTK_Trk_family                    -173.0    0.0023    1
CE00016     CE00016 GSK_glycogen_synthase_kinase       -239.0    0.0019    1
CE00288     CE00288 PTK_Insulin_receptor              -240.3       2.7    1

FIGURE 2C

```
Parsed for domains:
Model      Domain  seq-f seq-t    hmm-f hmm-t      score  E-value
--------   ------- ----- -----    ----- -----      -----  -------
CE00204    1/1       128   138 ..   515   525 ..     3.4      2.3
CE00031    1/1       120   175 ..   873   934 ..     0.7      2.5
CE00289    1/1       120   223 ..     1   109 []   -49.9   0.0045
CE00022    1/2       306   331 ..   191   216 ..     4.9     0.23
CE00288    1/1       125   353 ..     1   269 []  -240.3      2.7
CE00291    1/1       123   368 ..     1   285 []  -138.4     0.73
PF00548    1/1       370   378 ..   175   183 .]     1.6      7.7
CE00287    1/1       123   379 ..     1   260 []  -117.7     0.97
CE00290    1/1       124   379 ..     1   282 []  -173.0   0.0023
CE00292    1/1       123   381 ..     1   288 []  -102.3   0.0063
CE00022    2/2       414   437 ..   258   281 ..    21.6   2.8e-06
PF00069    1/1       123   439 ..     1   278 []   272.4   5.9e-78
CE00016    1/1        66   445 .]    1   433 []  -239.0   0.0019
```

FIGURE 2D

```
   1 GCAGAAAAGT ATAAAGATGG TAATCTCTGT AGGAAATTAG TCCCCATTAT
  51 TTAGCTGTAA AATTATAATT AAAAAAAAAA ATCTTTGTTT CTAAATCTTT
 101 GCCACTGATT ATTTCCTGAA AATACACTCC AGGAAGAAGC ATTTTTAAGT
 151 TAAAGCATGT GAACTCTTAT TTCTTGCTAC AGGTTCATAT TTCTTTTTCT
 201 AGAGAGTTTG CCAAATTATA CAACGTGCTC CTTCATGCTC TCACCAATCT
 251 TGGCTGTTTT GAAAGGCCAA GAATAATGTT TTGATTAAAC TGAATTTTTA
 301 AATTTCTAAC GAATTTGTCC GCTGTCATAT ATTTATTGAT CATTTGAACA
 351 TCTTTTTATT CTTAGCCTAT TTATTAAAGT ATTTTTATTG ATTTAGAAGA
 401 GCTTTTTATT ACAATATTTT AACCATTTGT CATATATATA TTGCATAGTG
 451 TCTTTTCTTT ATGATTTGTC TTTTGGAGGT AGCCTGTGAA TTGGTCTCCC
 501 TTTCTACAGG CTTAGTTAAT CCATTCTGCA TTAGAAAGAC TGATGTGGCT
 551 GTAAACCCTA CCTTTATATA TTGTGGTCAG AAGCCTGTAA CATAAAGTAT
 601 CAAGTCTTAA ACCAGTGATT CTCCAACTTT AGTGTGAATA AGAATCACCT
 651 TGGAGGTATG CTGACCAGAT TTACAGTCAG TGAGTATGAC CTAAGGCCCA
 701 GGGTTACCAT TTTTAATAAG AACTCCATAT TTGATACTGT TGATAAATAG
 751 ACCGTCCTTT GAGAAATAAT ACTCTTTAGC CTAGCACGCA GGGTTTTTAA
 801 TGATGCTATT CTCAGCTTAC TTATTTGTCT ACATTCCCCT ATGTGAAAAT
 851 TGCTCTTGCT GGGATTGTCT TTTTCCTGAG TAATGCATAG ACAATTCCAT
 901 CTCTAAGCCA TTGTGGCTAA AAGTGCCATA TGAATTTAAG ATGGTAAATAT
 951 GCCATTCTTC TCCCCCGGAA TTTCTTCTGT ATTCTACTTT TTCCAAATCC
1001 TGGCTTCCCT TAAGATGCA ACTCTATTTC CATCTTTTTT GTAATTATTC
1051 TCTGACCATT TTAAACAGAT TTTTTCCCCC ATCTCTGACT CTAAGCACTC
1101 ATGTGTTGTA ACCTTTTAGA ATTTCCTACA TTGTTGGATT TTGTTTCATT
1151 TTTATGTGAG TAATCTCAAA TTGTTCATTA TTTGTTGGCA GGGACTTTGC
1201 CTTATATAAT TTTTTTTTTA TCTCCCACAG GACCTGTGTG GATATAAAAA
1251 CGAATGCCCT TACCCTCATC CGTCTTGGCT ATTTGAAAGG CTATAGTGAA
1301 ATATTCACTG GGCATTCAGT GGATATTTTA AAAAATTAAA TCAGTCTGTT
1351 CATCCTGTCC ATAGCCTGTG TAATTCTGTA GACTTTGTTT ATATAATCTC
1401 TCAGCCTTGG TCATTGGCCA TTATCTATTG AAGAGACTCT CATCCTTTTA
1451 GTTTGTCCTC ATGGTGTTCA CTCCCATGTT TTGTTACTCT ATACGTTGTT
1501 TATGGCTTAG CAGCTCTAAT TCCATGCAGT ATTCCAGCTA AAGATTGTTA
1551 GTGCTAGTTT TTTCTAATAG AAGGATTTTG GACTTTTATG GGAAGGATGC
1601 CCTTAAGAGT ATGGTCACGT CTAGCTTATT GTATTGGTGA TCTCTCCCTG
1651 ACAGTTCCAA GCCAACTGAT CAGATCTCTA ACCTAGACTA CCCACAGTCT
1701 TACCCAAATA TCCTGAGTTG TTTCTCCAAT AAAATACAAC TTAAAGCTGA
1751 TGCTAGGGAA AGAGAACCGG GTTTCTGTAT CTCCCCAGCC TGGATTTGAT
1801 GCTAGCCCTA TTGGGTAGTA GTTGTAAAGA TGCTTCTATT TCTGCCTAAA
1851 CCAGCCCCCT GGGAAAAGA ATGACAGCAT ATTCTGGGGA AAGGAAAGGG
1901 GTTGGTGAGG GCAATCTAGT CAACATCCGT CACTCCATTG CTTGTTAGGC
1951 TTATTTTAGC CGATGTGTCT GACTGGGCAG GTGTCCCCTC TCTCCCTCAG
2001 TGCTCCATGT GCATCCCTCT TGAAGCTTCG CACTCTGTTG AAGAGGACAC
2051 TCATCCCAGG TAGAGAGGGG GACGGGAAAC TGGGCCAATT GAATCTATGT
2101 CCTTTTCTTT CCATCAGATC AAGGCCACTT AACTGGGATC CATTGACATC
2151 CTGAGGCCCA TGACCTTTGA AATTCCTTGC CAAGTTTTGT TTATGTGTTT
2201 CTTAGGAAAG AGAGTCCATG GCTTTCAGCA GATTTTCAAA GGGATCTCTA
2251 GATTAAAGCA CGATGGCACT AGATGATGGT GTTTTCTGTT GTTTCTTAGG
2301 TATTTCTCAA ACAGGAATGA CAGGAAATTA GAAATGCAAA GGGAAGTAGG
2351 GTGGTGGAAC TATTGTAATG CTAAACTACA GGATCCCTTT CTTATTTTAG
2401 GGGGATATAT TTTAGATGCC TTTGGCACAT GAGGCAGTCC TCAAAAGCTA
2451 TGTTTTCTAT TTCTCAAACA GGAATAACAA GGCTAGAAAT GCAAAGAGTA
2501 GAGGAGACAT GATAGATGCT GTGTGTAATA AAATTGGCCT GTATAATAGT
2551 GGTTTGAAAA TATTTTAGTT TTTGTCACTA ATGTTGTTAT ACAACCTTGG
2601 TAAATCATTT TTCTTCTAGG GATCTTAATG TAGTCGTCGG TAAAATGAAA
2651 GGGCTGGAAT ACATTTAAGG CTCCTTATAG CTCTAATATA CCTTTCATGA
2701 AGGAATTCTC TCTGTGCCAG GGATATCTAA AATGCTCTTA CATTACAAGA
2751 GAAAGGAATC CTTTTTGCCT GCCTCTGATT GTACCTCTGT GAGAGACTAA
2801 GACAGCTTAG ATACAGGTGC AGAAGGTAAA GGAACACTTA ATCAAGTAAA
2851 CACTAGACAT GAATTAATGA TTTGACTCAA GCTTTATTCC TTGGTGTGAA
2901 GTGCTTGACA GCAAACTCTA TAATGGGCCC ATTTGCTTGT TTGTTAAAGT
2951 AAAATTATTT CTTAAGCTTT ATGAGATAAA TATAAATGCT AATTCATCTG
3001 TTTGAATTTT TTTCTTATAT TGAGTTAGCT GTTTAAGAAT TTCTGAGAAA
3051 ATGTTTTGTT TGAACCACAT TATTGCAGAA TGAAGAGAAT AATTTGAAAT
3101 CTTTTAATGT GTTTGCAGTC ATTATTTAGA AGCAAGGTCC TTGAATGAGC
3151 GAGATTATCG GGACCGGAGA TACGTTGACG AATACAGGAA TGACTACTGT
```

FIGURE 3A

```
3201 GAAGGATATG TTCCTAGACA TTATCACAGA GACATTGAAA GCGGGTATCG
3251 AATCCACTGC AGTAAATCTT CAGTCCGCAG CAGGAGAAGC AGTCCTAAAA
3301 GGAAGCGCAA TAGACACTGT TCAAGTCATC AGTCACGTTC GGTATGATTG
3351 GTTTTGTTTT CAATTTGAGT GGAGTTTTAT TTGTGTGTAC TCTTAACGAG
3401 CTGATAAGTT TCTAATTTTT TATATATATA TATATAAAAT ACTATTTGGA
3451 TATATTATAA TTGTATTTAT ATTACTTAAA TCCTTAAAGG AAACCTCCAA
3501 ATTCTTGTAG CTGATCTGTA TATTTATTAG CTAGCCCTCA TTTGCCCACA
3551 TTTCCTCATA TTCTGCAGAC CAGATAATGA GTTTATTGAT TTTAATAATA
3601 AAACTATTTT TTTATTTGTA ACATATTCTT ATGAAAAAAT CATGCACCCA
3651 TATCTTTTCT TTCATCTTAA GCATTTTTTT TTTCTTAGAA ACCCTTTATC
3701 TGGTACTTGA AAATAAATGT GAAATATTGC ACTGGTGGAC ACCTGAATGT
3751 TACTAACCTG CATAGAGCAT AGTTCCATAG TCCAGTGCAT CATTGTCTGC
3801 AATGAATTCT TTTGAAGTTG TGAAAATGGG TGCTGAATGG GAAACATCCA
3851 AAAAGTCTGC CCCCCCCTTT TTTTTTTTAA CACTCAGACA TCTTCACCTG
3901 CTTGAACAGT GAACTTTGAA TTAGTTTCTC CCCAAGTTTT CTTCAGTAAA
3951 ACTAGTTTTT ATTAGATTGA ACATTGAAAT TAACTAGCCT TTATTTTCCC
4001 CTTTTATTTT AATCATGTAT ATTTTAAAAT ATTGCTAAAT TAGAATAATT
4051 TCAAATAGTC TTGACATTTT AAAACATTTT TCTGAAAAAC TAGACATCTC
4101 AATTCACAGC ATATGCTGTT TATAGCAAGA GATAAGTAAA TCATGACATT
4151 GCATTCTTTA AATTTCAGAC TTCAATTAAA TCAGTATTTT AAAGAGACAA
4201 TTGTGTTGTT TTTTTCTATT GCCACTTTAA GTATCTTATC TGAAAATCTG
4251 TTCCTTGCCA TGTTTTTCTT CTGTAACATA AACTGTGCCC TGTGAATTTC
4301 TGGGGACTGA ATTTGAAATT GCTCCTGCCA ACTGTTCGTG GCCTGGTGCT
4351 TATCTGAATG CCTGAATATC TCCCCGCTGA ATGAATTGCG TATTCTGCCC
4401 TGAATTCACT CTGATATATT GATTGGCTGG ACGATCTTGG TGCTGCCCAC
4451 TTGCCGTTCC AGAAGAGCCA CCGAAGGAAA AGATCCAGGA GTATAGAGGA
4501 TGATGAGGAG GGTCACCTGA TCTGTCAAGA TGGAGACGTT CTAAGAGCAA
4551 GATGTATAGA ATATTTTTCA ACACTTTTTA AACTTTGCAG AAAGAATAAT
4601 CTTTTTAAGA ATAGTTTGTC AGCGGGGGGC TAAAGAACTC TTCATTGCTT
4651 TTTTATTTTG CTTTTTGTGG GTTTGTTTGT TCTTTTATAT TTCTTCTTTT
4701 CTGTAGAATT TAAATATTTC TATTCTAAAG TTCCAAAATA ATCAGTGGAA
4751 TTTGAGATTA GAGCAAGAAA GATAGCTCTA TCTAATTGTT TTTGTAGCAG
4801 CTGAAACTAA AATAATTTGA GTGCTGAAAC CTTAGTTATG CTTTGTTAGA
4851 GATCATTTGA AAATATTCCA CACTTAAGCA TTCATTGTTT GAAGAACTAG
4901 ACAGTTTGTA CTCAGGTACT TACACCTCTT TTTCCCTCCT CACTCTAGAT
4951 GAAATCGTGG ACACTTTGGG TGAAGGAGCC TTTGGCAAAG TTGTAGAGTG
5001 CATTGATCAT GGCATGTAAG TTTGTTTTTT CCTTTTCAAA CATTCTGATG
5051 TTTTTGGTGG GGAAAGATTC ATAATTCAGA TGAAATTTTA TTTATTTATT
5101 TATTTGAGAT AGGGCCTCTG TTGCCCAGGC TTGAGTGCAG TGGTGCTATC
5151 TTGGCTCACT GCAACTGCCG CCTCCCGGCT TCAAGTGATT CTCCTGCTTC
5201 AGCCTCTCAA GTAGCTGGGA TTACAGGAGC CTGCCACCAC ACCTAGCTAG
5251 TTTTTGTATT TTTAATAGAG ATGGGGTTTC ACCGTGTTGG CCTGGGTGGT
5301 CTCGAACTCC TGACCTCAAG TGATCTACCC GCCTCAGTTT CCCAAAACGT
5351 TGGGATTACA AGCCTGAGCC CCTGTGCCCG GCCAAGATGG AATATATTTT
5401 AAATGGTAGC CACGTGTTTT GGGGGGTAAA TTACTCACCA AAGTTTCTTG
5451 AACTTTGTAT GATTTATTTA CCGTGAATGT GGATCTTAAG AATGCTGACT
5501 GCCGGGCACA GTGGCTCACT CCTGTAATCG CAGCACTTTG GGAGGCCAAG
5551 GCAGGTGGAT CACCTGAGGT TGGGAGTTCA AGACTAGCCT GACCAACATG
5601 GAGAAATACA TTCTCTACTA AAAATACAAA ATTAGCCAGG TGTGGTGGCA
5651 CATGCCTGTA ATCCCAGTTG CTTGGGAGGC TGAGGCAGGA GAATCACTTG
5701 AACCCAGGAG GGGAGGAAGG CGGAGGTTGC GGTGAGCCAA GATTGTGCCA
5751 TTGCACTCCA GCCTAGGCAA CGAGTGAAAA TCCGTCTCAA AAAAAATAAA
5801 AATAAAAAAA AAGAATGATG ACAAATTTCA ACAGGGGGAA ATCATTGAAA
5851 TTAAAGTGGA TGTTCAAGTG AAGGAATTTC CCAGAACTCC AGAACTGAGG
5901 CCCTTGACCC TGTATATAAG ATTTGGCAAT TTCGGATTAC AGAGGCAATA
5951 AAGCATGTCT AATCTTAAAT GTTAAGAGTT AGCTTCCTAA ACTATAAAGA
6001 CATTTTATTA TCTAGGGCCT AGAGAATAAA GTTTGTGATT TGACCCTTTC
6051 TGCCTCATTT TACCGTTTTC CTCTAGGACC TCTATTTTGT GGCTTGAAAA
6101 CTTTTGTAAG AGAAGCTCTT AGAACTTTTG CGAAACTTCA CATTTCTAAA
6151 ATGACAAAAT TTTTTATCAT AAATTATTTG GGAAGGATGT AATTTCCAAC
6201 CTGTTGTAAA TATTAATATT AAAAAATAAA ACTTACCTCT CTCTAAATGC
6251 ATTTCAGGGA ATCTAAATAC CATAGCAGCT TGATACCTAC CATCATCCAT
6301 AAACAAACTC TTCTTGAATA CTTAGAAATG TTTTATTATT GAATTTATTG
6351 TCATTTCACT TTCCATAAAT ACTATCCTAA ATTATCCCCA CATTTTGCTT
6401 TTCTGCAACA AATATGTGAA TGTAAATTGA ACTTTAAAGT ATTTTGAAAT
```

FIGURE 3B

```
6451 ATTTTCAGAC TTACAGAAAA ATTGATAAAA TAGTTCAAAG AATTCCCATA
6501 TATTCCAAAT GTTAACCTAT TTTCCAAATG TTTACATTTT ATAAGATTTG
6551 CTTTATCATT ATACATACAT TTGTTTTCAA ATTTTGCCAA CTAATCTGCA
6601 GACTTTATTC AGATTTCACC AGTCATCCCA TTAATGTCCT TTTAGAATTT
6651 CTTGAAAGTC TAAGTCTTGG TGTATTTAAT GAAATGTATC TTAAAACAAA
6701 TTTTTTTTTA ATGAGATGGA GTCTCACTGT GTTGCTCTGG CTGGTGTGGA
6751 ACTCCTGGCC TCAAGTGATC CTTCTGCCTC AGCCTCCCAT AGTGCTGGGA
6801 TTACAGGGTG TGAGCCCTGT AGTCACGTGT GGCACACACC TGTACCACAT
6851 CTGGCCTGGA ATGTTTTCTT TATTGGGGCA GTTGAGGCCT CTAAAAAATG
6901 AGTACATATA GCCATAGATA AATATCTGAC TGTCTAGCAT TGTATGTTTT
6951 CTTTTTTCAT TTTCGTGGAT ACAAGCACTG AGAAAACTTT TTGGTCATAT
7001 AATTAAATAG ATAGGAGTAG AAGCTTTGTC ACAGTAATCT TATTAGAGTT
7051 CTTTTAAGTC TTGAGGTATA TGCCAAGCAT TAAAAAATTT TTTTAGTGAC
7101 TTATCAGTTC ACATTCGTTG GGGCCTTGTT GAAAGCAATG AACTGGAAAC
7151 CACTGGATGT GGAAAAAGGT TTTGTATCCA GCCATTAGAA TACGTGTTTG
7201 TTTGCCCCAA ATGTTTTTAT AGCCTAGGGC ATACATCCTG TTACACTAGT
7251 AAGAGATGGG TATGGTTTTG TAAAGTGGAA GGGTCATAGT GAAAAAGAAG
7301 GCTTGAATGC TGGCTCATCT GTAGGTAGAT TAGGTTTAAA AAGGAAGACA
7351 AAAATAAATT GAAGATTTGC AACATTTATG GCTCTATACT TTTTAGGAAG
7401 CATTCTTACA GATGCCGCAG TCTAAAGCCC ACTGCCCTCC CCTGTAGCTG
7451 TTTCTGTATA CTGGCATCAG TGCATCTGCT AAGGTTTTTC TGGGCTTCAT
7501 TACTTAGAGT TGGGGTCTCC TTTACCTGGA TGTTTCCTTC CCAATCTGAC
7551 AAACTCCCAG CTATCTTTCA GGACTCAGTT CTGTGTCACC TCTTCTGTGA
7601 AGAAGTCTAA GTTGTTTCTG TGTCTGTCTT TTCCATTAGA CTTTGAAGTA
7651 CGTAGGGACA CACCCCGTCT TTTAATCACT AATATCTGTG CATTGCCTGG
7701 CACAGAGTAG GCCTAGCCTG GTAAATGAAT GAATGCTTTC AACAGTAGCA
7751 TATCCTATTT TTGGTTTACA TTTGTATATA TCTTTTAAAA CTGTTGTTGT
7801 ATAAAATGTA ATTAAATTTA AAATTCTAGG AGCAAACGTT AAAACTCATA
7851 AGTATTAAGG GAATTATCAC TTCATATAAA GTATTTTATC AAAATGTTTT
7901 AAGAAGATGT TATATGGAAT CTGCTATAAT ATGTTCTGAA AGATTATTTT
7951 AAATGGCATA GAGGAATTGG TAATTAAGAT TATGCTTTAG AGCATAACAT
8001 GGCTTCAGCT CACTCTTGTA CATTTATCAT TTTTATCTTA ATTTTATTTT
8051 TAAGGGATGG CATGCATGTA GCAGTGAAAA TCGTAAAAAA TGTAGGCCGT
8101 TACCGTGAAG CAGCTCGTTC AGAAATCCAA GTATTAGAGC ACTTAAATAG
8151 TACTGATCCC AATAGTGTCT TGTAAGTATA ACTTTCACCT AGGAGCCATC
8201 ATATTACATG AAATATTCAG GTTTCCATAA ACTGAATTAT TATTTTGCTC
8251 TGTTTTAGCC GATGTGTCCA GATGCTAGAA TGGTTTGATC ATCATGGTCA
8301 TGTTTGTATT GTGTTTGAAC TACTGGGACT TAGTACTTAC GATTTCATTA
8351 AAGAAAACAG CTTTCTGCCA TTTCAAATTG ACCACATCAG GCAGATGGCG
8401 TATCAGATCT GCCAGTCAAT AAATTGTAAG TACACTTGAT AAATCTTTAT
8451 TTTTATTTAT TTATTTATTT ATTTATTTTG AGACGGAGTC TCGCTCTGTC
8501 ACCCAGGCTG GAGTGCAGTG GCGCTCTCGG GTCCCAGCAA GCTCAGCCTC
8551 CCGGGTTCAC GCCATTTTCC CGCCTCAGCC TCCCGAGTAG CTGGGACTAC
8601 AGGCGCCCAC CACCATGCCC AGCTAATTTT TTGTATTTTT AGTAGAGATG
8651 GGATTTCACA GTGTTAGCCA GGATGGTCTC GATCTCCTGA CCTTGTGATT
8701 GCCCCCCTCG GCCTCCCAAA GTGCTGGGGT TATAGGCGTG AGCCACTGTG
8751 CACAGCAATA AATCTTTATT TTTAAATATT TTTTATGTTT GTACCTCCTT
8801 AACAATTAAG ATAAATCTTT AAGCACCAGA AAACTTGTTT TTATTATACA
8851 AGCTATATAT CCAAATGTTG TCACTAAAAA AACAGACATT TTACAAGTAA
8901 AGATGAATCG TCTCTTGACC ACTATATCCT TTGCCAGTCC TCCTTTCCCT
8951 CCTAGTACAA ATTAAGTTTG TAAGTGAAAC TAATAATGTG CTTTTGTTCT
9001 CTTGTAGTTT TACATCATAA TAAATTAACC CATACAGATC TGAAGCCTGA
9051 AAATATTTTG TTTGTGAAGT CTGACTATGT AGTCAAATAT AATTCTAAAA
9101 TGGTAAGTTA AAGACTTGTT TTAATTTGGG TGGTTGTCTT TAAAATTAAT
9151 TTAACTTGAT GATCTTTGGA TGAGGAATTT CACTTCTGAG CCTTATTATA
9201 TCCTGTTGTT TAACCAAAAA GAAGTAATCC TTCTTTGCCT TTCTCATGAG
9251 CTTACTTTGA CAATCAAGAA GATAATTCAT GTGCTGGCCT TTTGAGTAGC
9301 GCTATAAAAT GTATCTATTG AGTTTCATGT TTACTCAACT GTGTCTCTCT
9351 AGAAACGTGA TGAACGCACA CTGAAAAACA CAGATATCAA AGTTGTTGAC
9401 TTTGGAAGTG CAACGTATGA TGATGAACAT CACAGTACTT TGGTGTCTAC
9451 CCGGCACTAC AGAGCTCCCG AGGTCATTTT GGGTCAGTAG ACACCAGGCT
9501 TTCTAATATT ATAATTGAAG AAGAGATTTT TGTTCTTTAC AGCTTTACTG
9551 GTGGGGTGGG GAAGTATGAT CTTCTCAGCA GGATTCAGAA AACGTTTTCT
9601 ATTTTCATAA AAAATGTGTG GACATTGCTA TAAATACTTT TCCTGAGTGG
9651 TAAACATGTG ATACTGTCTG GGAAAGATAT TCCAGGTGGT GGTTATTTTT
```

FIGURE 3C

```
 9701 GAACAAGTAA ATCTTAAATG ATCATAAGAG AACAGGCTGT GTTAGCTAAA
 9751 TGCATCAAAG AAATGTGATT TTGAAGTTAT ATGAGTACCT ATTTTCATGC
 9801 CATCACAAAA GCACATGGCT GGTAAAAATA CTGAGGAAAC TGGTTGGCAG
 9851 ATGTCTAGAA TATAGGATGG ATAAAGGTCA AGAGAAGAAA GAGGCTTCTC
 9901 TAAGAGCTCC TGTGATAACC CTTGATGTGA GAAAGTCTGG GAAAGAAAAT
 9951 GAGTTAAGGT GCAGAGTTTT CAAATAAGAA GGGACTTATT AAGGGAGTGT
10001 TATGCCTCAA CATTAAAAGT TATAGATCAG GTGTGTTAAT AAATCAGGGA
10051 AGTCAGAGAT TGGCTTGGGA GCTTGGAGAC ATTGGGAAAC ATTCAGATCA
10101 GGCATATCAA GAGAGTTGAA TGTAATAAGC TGATTACTTA GCCTAAAGTT
10151 AGGTCCAACT GAGGTTAGAT TGTAAAGCAT TTTTGTGGAA TCGTATTTTA
10201 ATACTTTTTA CTTTTTTTGT GTGTCCAACG GGACTTGGTA GTTCAGAATA
10251 GGAGTGTAAA AGCAAACTCT TGATACTTAC CTAGAGTAGA GTAGTAAAGG
10301 AGTGAGGAAA TCAAGAATCC TGTGCAGCTC TTGCCCACAG AACTTCCCTT
10351 GATGACAGAA ATGTTCCATT TCTGCACTGT CCCATATGGT AGCCACTAGT
10401 CACTGTGCGT GACTGACTAC CTTGTAGTGG GGCCAGTGTG ACTGAGGAGA
10451 ACTGAGTTTT GAATTTACAT TAATTTTATT TCAGATTTAA ACAGCCACAT
10501 GTGGCTAGTG GTTACCATAT TGAACAAGCA CAACTCTTAG AGCTTGTCTT
10551 TTAAATGCGT AATAATAGGG TTTCTGCGTA GTACAAATTG AAAGGAGCTA
10601 CTGTGTAAGG GTAAAAGAAA GCAATATGGG AAGAGATAGT GGACAGAGAG
10651 GTATTTTCAG AGATTAGAAG GCAATAGATT CCTCATTTTA AGAATCAGAT
10701 TTTTCCCCAA ATATTTGGCA TTTTTTCTTT GTTATTGGTA TATCAAACAG
10751 TGGTGCATCG TACAGTGTGC TATCCTAGAT TGAGTAAAAT ATAGTATATA
10801 GTAACCCCCC CCTTTTTTTT TTCTTTGAGA TGGAGTTTCA CTTTGTCACC
10851 CAGGCTGGAG TGCAGTGGTA CCATCTCGGC TCACTGCAAC CTCCACCTCC
10901 CAGGTTCGCG CGATTCTCCT AACTCAGCCT CCTGAGTAGC TGGGATTACA
10951 GGTGCCCACC ACCACACCCG GCTAATTTTT ATAGTTTTTA GTAGAGATGG
11001 GGTTTCACCA TGTTAGCCAG GCTGGTCTCG AACTCCTGAC CTCAGGTGAT
11051 CCTCCTGCCT CGGCCTCCCA AAGTGCTTGG ATTACAGGCG TGAGCCACCG
11101 CGCCCGGCCA AGGATTTTTT TTTTTTAATT TTTATGTTTT TTATAACAGA
11151 GACAGGGCCT CACCATGTTG CACAGGCTGG TCTCGAACTC CTGGGCTTAA
11201 GTGATCCGCC TGCCTTGGCC TCCCAAAGTG CTGGGATTAT AGGTGTGAGC
11251 CACCGCACCC ACCAGAATAT GGTCAATCTT ATTAATAAAG TTCCAAATGT
11301 GGCCAAGCAA GGGATAGTAC AAATCTGAAA TTGGAGTCCC TGGCCTTGAG
11351 GAGAAAGAAT CAGGAGATTG GGAGAATAGA AAGGTCCTTT GTTTGTGGAG
11401 TGAGGATGAA GGCATAATGC AATTGGAGGG GAAAATGTAG TCAGGTGCTA
11451 GAGTTGAAGT AGGCAGTTGG CCTTATGTTG GGTATAAAAG CTAACTCATC
11501 CAAGAATGAG ATGATTTAGA ATGGTGTACT GCAGAAGATT ACAGTCACCT
11551 GGGAAAAGAC TAAATTGGGA GATAGGAGTG GTTGAAAAAT AAAACTTTTT
11601 TTTTTTTTTG AGACGCAGTC TTGCACTGTC ACCCGGGCTG GACTGCAGTG
11651 GCACGATCTC GGCTCACTGC AACTTCTGCC TCCTGGGTTC AAGCGATTCT
11701 CCTGTGTCAG CCTCCCAAGT AGCTGGGCTT ACAGGTGCCC GCCACCACGC
11751 CCAGCTAATT TTTTGTATTT TTAGTAGAGA TGGGGTTTCA CCACATTGGC
11801 CAGGCTGGTC TCCAACTCCT GACCTTGTGA TTCACCTGCC TTGGCCTCCC
11851 AAAGTGCTGG GATTACAGGT GTGAGCCACC GTGCCTGGTT GAAAAATAAA
11901 ACTTTTATGA GGTCCAAGCT CTAGCATTTA CGGATTTTGT ATGTGTTAAT
11951 AGGTAGAAAC CATGCTCCAT TATTTATTTA TTTTATTTTT GAGACAGAGT
12001 CTCACTCTGT TGCCTGGCCT GGAGTGCAGT GGTGCAATCT CAGCTCACTG
12051 CAACCTCTGC CTCCCGGGTT CAAGCGATTC TCCTGCCTCA GCCTCCTGAG
12101 TAGCTGGGAT TACAAGTGCA CACCACCACA CCCAACTAAT TTATATATAT
12151 ATATATATAT ATATTTAAA ATTTTTATTT TTATTTTTG TTATTTGTTT
12201 ATTTATTTTT TTGAGATGGA GTTTTGCTTT TATTGCCCAG GCTAGAGTGC
12251 AGTGGCGCAA TCTCAGCTTA CTGCAACCTC TGCCTTCCGG TTTCAAGCCA
12301 TTCTCCTGCC TCAGCCTCCC AAGTCACTGG GATTACAGGC GTCTGCCACC
12351 ACGCCCAGCT AATTTTTTTG TATTTTTAGT AGAGACGGGG TTTCACCATG
12401 TTGGTCAGAC TGGTCTCGAA CTGCCAACCT GGTGATCCAC CCGCCTCGGC
12451 CTCCCAAAGT GCTGGGATTA CAGGCATGAG CCACCGCGCC TGGCCCATGC
12501 TCTATTTATTA TCCATTTTGTT CAAATGACAG ACACTGAGGC GGATGGTTAA
12551 CAAAAATGAC TTAAGTCATT ATATATTGAC TTGAATATAT TTCTTCTTTT
12601 ATCTTTAACT TCAGTGATAA TGAAAGTAAT TGAAATGTCT TTGAATGTAG
12651 ATTTTATTTA TACATTTTTT AACTAAATAT TTGATCTTTG AAATATTAAA
12701 ATATCTATGT GGTTGGTTCT TTCTCCTTCC CAGTCAGTAT AGATTTAAGA
12751 AGGCTAGATG TTTTATTCTG ATCTGAATAA TACTGTCATT GAGAATTCTG
12801 AAGGAGAAAG TATATAAAAT CATGTATAGA CAGCGCCGAT GTTTATGTAT
12851 AGATCCCTCT CTGAGCTCCA ATGTGTCTGT AATTTCTGCT TATAGGTGAA
12901 ACTGCTTAAA ATTCCCATTA TACCTTTTAT ACAATTTGTG CAAAACGGTA
```

FIGURE 3D

```
12951 ATATTTCTCT TAACGGAAGA AGTAAACTCA TGCATCAAGC TGATGATAAT
13001 TGATAAGGCA TTAGTAATTT CATTCTGAGG ATAATTATAA ACCTGTATTT
13051 GTGCTAATAA AATATAAAAA TTCTTGGACT AACCATGAAC TGAGCATAAT
13101 AATGGTTTTA ACAGCAGTGC TCTCCCATTA TATAAACAGT TCAGAGACTA
13151 TGGAATATTT GCACGAATTG GTTGTATACT TGGAAAATGG TAGCCCCCTT
13201 TTATTTTACA TAACATGCAC CCCTCCCTAG TTAGAATACT GTGTCTTGAT
13251 GTGAGCATAT GGACTATGGA GTGTGTTGAA TAGCATTTGC TGTAAAACTA
13301 GAACTATAAA CTCTGAATTT GGTGTCTTAT TCTCCCAAAT GGGTTCTGTA
13351 AAGGGAGCAC TCATATAGGG AAGGATTTAA TGTACTGTCA ATTAAAAGTT
13401 TTTGCATAGT AAAATGTTTC TATTTGTTTT AAAATAGCTT TAGGTTGGTC
13451 TCAGCCTTGT GATGTTTGGA GCATAGGTTG CATTCTTATT GAATATTACC
13501 TTGGTTTCAC AGTCTTTCAG GTACGTGGCT AGTAAATTCC ATTTAATAAT
13551 TCATAACAAA TTGTAAACGT TAAAGGTATG CTAAAGTTTT GACTTCCATA
13601 TTGGAAAATT GCCATACATC ATTATTCTTG AGATTAAAAC TTAGGCAAAA
13651 TGGTCATTCT TTAAAACCAC AGTTGAATGA AATATTACTA TGAGTGAGTG
13701 ATCATAGTTA ATTTTGCATG TGATTAGTGT TTGTAACACA TGGTTCATAT
13751 ATGGTTCATA CTGTCTCCTT TTTTAAATTG TAGAGCTTCT TCATAAATTT
13801 GCAGTAGTGT TAATGTGGCC AGTTTTCAGT TATAGTTATG TTGACTATCA
13851 ATATGGCCAT GAACGAGTCA CTTATTCCTT TTTATAAAAG AATTCAGGAA
13901 CAACAAGGGA TTGTATTTTA CTCTTAAGTA TTAAGCATCT ATAATGTCTT
13951 AGGCATTTCT AAGTATAAGT ACATAAAGGT GAAGAGACAA CATCTTTCTC
14001 AAGTCATGCA AAAGACATTG GAAAGTTATC GCAGTATAGT GTAGCATTTG
14051 CTGTGATGGA ACAACGTAGA AAGTGTAGGT AGGGAGGGCC AGGCGGGGTA
14101 GCTCACACCT GTAATCCCAG CACTTTGGGA GGCTGAGGTG GGTGGATCAT
14151 GAGGTCAGGA GATCGAGACC ATCCTGGCTA ACATGGTGAA ACCCTGTCTC
14201 TACTAAAAGT ATAAAAAATT AGCTGGGCGT GGTGGCGGGC GCCTGTAGTC
14251 CCAGCTACTC GGGAGGCTGA GGCAGGAGAA TGGCGTGAAC CTGGGAGGCG
14301 GAGCTTGCAG TGAGCGAGAT CATGCCACTG CACTCCAGCC TGGACAACAG
14351 GGTGAGACTC TGTTGCAAAA AAAAAAAAAA AAAAAAAAAA ACAAAGTGTA
14401 GGTAGGGAGA ACCCAGGAAA GGTTAATAAT TACTTTAGAG AAGGCGTCAC
14451 TGAGAACATA GGAAGAGGAG GAGGAGTTAG AAAACTGGAG TGCAATGGGC
14501 ATATAAGGAA GAAGAAATAG TATCTGTAAA TGCACAGAGG AGTAAAGGAA
14551 CATATTCTAC TCAGGGAAGA ATAGCGTTGT CAGAGTGTCT TGTATAAATG
14601 GGAAAATTAT AACAATAGGC AAGGATCAAT TCATAAAAGA CTTCGCAAGG
14651 TATTGGTTTG ATCCTAGAAG TCAGTGGATT CCAAAAGTAG ACTGGTCCAA
14701 AATGAAAATG GTTGTCTAGG TTTGCCATTC TGACCCTTAT TTAGAGATTA
14751 TCCCTCCTGC TTTTTTTTTT TTTAATGTCT CTTTTATGTA ATGATAGTCA
14801 TAGTTGTTGG TAGTTTGCTT TTAAAAATAA AAAGTCCTTA ATTGGTAAAA
14851 CAAAAAGTAG GAAACTCTAC TTTCTTTTCC ACTCTGTCCT TAAGTTGTAC
14901 TTACATCTGA AATCTTAATT TTTTTTTTTT TTTCCCTGAG ATGGAGTCTC
14951 ACTGTGTCAC CCAGGCTGGA GTGCAGTGGC GCAACGTCAG CTCACTGCAA
15001 CCTCTGCCTC CCGGGTTCAA GTGATTCTCA TGTCTCAGCC TCCCAAGTAG
15051 CTGGGATTAC AGGCACGAGC CACTACACCC CACTAATTTT TTGTATTTTT
15101 AGTAGAGGGT TTTGCTGTGT TGACCAGGCT GGTCTCGAAC TCCTGACCTC
15151 AAGTGATCTA CCCTCCTTGG CCTCCCAAAG TGCTGGGATT ACAGGTGTGA
15201 GCCACCGCAC CCAGCCTGAA ATTTAAATTC TTGAAAGCTT TAGGTGATGC
15251 AACCATTGAA GAACTTTAAA TAGGGTCATG GTATGATCGA GGTGTTGTGT
15301 TGTTTTGTTT GGGGAAGAGG GGCTGGAGAT CCCAGCTAGT ACTGTTGAGG
15351 TTGATTTGAA GTTAGAGCAG TGCAGGGGGC ATGCAGCTAT GATGGGCTAA
15401 GAGTCACTTA GGCAGCTGTT GCACAATGAT GAATTCCCTG TTCGTGGGGC
15451 ACCTCGCCAG ATTTCTGTTT CTGTCTAATC TGTAGAGATC CTGTTGAAAA
15501 GTACTCTGAG TTTATAGATA AGTTTGATGT CTTAGAATCA TGGTTATTAA
15551 TCAGTTCTGG GAGGTATTGT CTGGTTTTGC AGTGGTGAGC TGTAGGGTCA
15601 AGAAAAAGTT AAGCAAAGTG AATGCTTTCA TCAATCTGAC TAATATGAAA
15651 TGGATGCTTC CGGTGATTTT GTGATTATAA ATCACTTTGA GTTTTAAATG
15701 AAGTATATAT TATTTGAGAG GTGGTTTATA TTTTAACTCC ACCCTGCAAA
15751 ATACTCTTAA ACTAAGGAAT TTCTTTAAAA TGTGAAGCTA GTATTACTTA
15801 TTCCTGTCAT GTATCACAAC GATTTGGAAG CAATATGCAA GGCACAGTAG
15851 TTGATAGATT TCTTTTAAAA GTGTTGCATA CAGCCTCTGC TCTCCAGAAC
15901 AAGGGTTAGC AAACTTTGGC CCATGGTGAA ATCCTGCCTG GTGCCTGTTT
15951 TTACAAAAAG AAGAAGAGTA TGCAATAGGG ACCACTCATG ACGAGCCAAG
16001 CCTAAAATAT TTACTATCTG GCCCTTTACA GAAGTTTGCC AACCTCTGCT
16051 CTAGAAGCAT ACCATTCCAG CTGTAAGTTT GACCGTTTTC TGTATTCTAC
16101 TTCAGCCAAG CCTCCGTTAC TAATTTAAGG ATATGTGCTT TGACATGGGT
16151 TGATAGCTTA ACTTTCCTCA TATATGAGCT ATATGACTTT GAGGTAGTAT
```

FIGURE 3E

```
16201 CTTAACCTTT TTGAAATTCA TGTTCCCACA TACCTAGCTC AGAATTGTTT
16251 AGAGAATTAT TGGGACTGTA TGTATGTCTG TTGCCTGGGA GTAGTAAGTG
16301 TTAACAAGTG AACTATTCAT TGGGTACTGG ATGTTAATTT TGGTTAAGCA
16351 GCTGATTAAA TGAGGAGACA GTTTTTCTGG TAACCTTGCC CAGTTATTCT
16401 TTAAACAGTG TAAGAAGTGC AAATAAAGAA GGAAACTAAA ATTTTAGATT
16451 AAACAAGTTA ATGTGTTTGT AGGGAAATGG AGAGTACTAA ATTTCTTTTT
16501 CTTACATGTT TTAGACTCAT GATAGTAAAG AGCACCTGGC AATGATGGAA
16551 CGAATATTAG GACCCATACC ACAACACATG ATTCAGAAAA CAAGGTATGT
16601 TTTAAGATTC AAGACTTTTG TTGGATATGT GCAATAGCAT ATATTCAAAC
16651 TACAGAAAAC CCAACGTTGT TGTAATACTG ATTCCAAGGA CTATAGATTT
16701 TGACTTTTTT TTTTTTTTCT GTACTGGAGG TAACTTCTAA CTTCATCTTA
16751 CTCCTTTTTT TTTTTTTGAG ATGGAGTCTC ACTCTGTCAC CCAGGCTGGA
16801 GTGCAGTGGC ACGATCTCAG CTCACTGCAG CCTCTGCCTC CTGGGTTCAA
16851 GTGATTCTTC TGCCTCAGCC CCCTGAGTCG CTGGGATTAC AGGTGCCCAC
16901 CACTATGCCT GGCTAATTTT TGTATTTTTA GTAGAGATGG GGTTTCACCG
16951 TGTTAGTCAG GCTGGTCTTG AACTCCTGAC CTCAGGTGAT CTGCCTGCCT
17001 TGGCCTCCCA AAGTGCTGGA ATTACAGGTG TGAGTCACTG CACTAGGCCA
17051 TGTTTTTAAA AACTAATATA ATAAAAAATA TTTACCTTGT GATCTAGTGC
17101 AGGGGTCCCC AACCCCTCGG AACTGGGCTG TACAACAGGA GGTGAGTGGC
17151 GGGTGAGTGA GCATTATTGC TGCCTGAGCT GCACCTCCTG TCAGATCAGC
17201 AGTGGCATTA GATTCTCATA GGAATGTGAA CCCTATTGTG AACTGCGCAC
17251 GTGAGGGATC TACGTTGCAT GAAGGTTCCT TATGAGAATC TAATGCCTGA
17301 TGATCTGAGG TGGAAGTTTG ATTCCAAACC ATCATCCCTC CTCCCCGGAT
17351 CTGCTTCCAT GAAACCGGTC CCTGGTTCCA AAAGGGTTGA GGACCACTGA
17401 TCTAGTAAAC AAAATGGCTT TTGGGTTTTT TTTGTTTTTT TTTTTTTTTT
17451 AACTCAAGTT TACGTTTGGC ATAAGTGTTT TCTTAGGCGA TGTAAAAATA
17501 ATACATAGAA TATGGAAAAG CTTGTGTTTT GGAATCATAT CACTCTAAGT
17551 GTGAAATTTA TTCTGTCCTT AACCAGCTGT ATATTCTTAG ACAAGGTGGT
17601 ATTTCCAAAC ACAGCTTCAT CGCAGAAGCC ACCGAGGGAG TTCTTTAAAG
17651 ATTTCCAGCC CCATTCTAGA TCTAGTGAAA ACAGAATTTT AGGACTGGAT
17701 CCAGGGGGCC CCTAGTTTTA AGCTGACATT GTTCCATATG TGATAGGAAC
17751 AACTTAGTTG AGAGACTAAA ACCTCACAGG GTGGAGGATA TGAGGTGTCC
17801 GATATATAAT TGTTGCTGAG GTTTTTAAAA ATTGTATGCA TCTATATTAT
17851 ATAAGTCTAT ACACTTAGAG AGAGCTGCTT TCCATGTCTC CCCTCATGGG
17901 TGCAGGGTAA AGATACGACT CTTGTTATTT TACTAATCCA GACTTTTTTT
17951 TTTTTTCTGT AGAAAACGCA AGTATTTTCA CCATAACCAG CTAGATTGGG
18001 ATGAACACAG TTCTGCTGGT AGATATGTTA GGAGACGCTG CAAACCGTTG
18051 AAGGTAAAAG AAAAAAGATT AAAGGTTAAA TAAACCACGT GTTTGCACTA
18101 TTAATAATTT TTTTTAAAAC AAAAACATTT CTCCCCCAGG AATTTTATGCT
18151 TTGTCATGAT GAAGAACATG AGAAACTGTT TGACCTGGTT CGAAGAATGT
18201 TAGAATATGA TCCAACTCAA AGAATTACCT TGGATGAAGC ATTGCAGCAT
18251 CCTTTCTTTG ACTTATTAAA AAAGAAATGA AATGGGAATC AGTGGTCTTA
18301 CTATATACTT CTCTAGAAGA GATTACTTAA GACTGTGTCA GTCAACTAAA
18351 CATTCTAATA TTTTTGTAAA CATTAAATTA TTTTGTACAG TTAAGTGTAA
18401 ATATTGTATG TTTTGTATCA ATAGCATAAT TAACTTGTTA AGCAAGTATG
18451 GTCTTGATAA TGCATTAGAA AAATTAAAAT TAATTTTTCT TTTTGAAATT
18501 ACCATTTTTA AATACCTTTG AAATATCCTT TGTGTCCAGT GATAAATGTG
18551 ATTGATCTTG CCTTTTGTAC ATGGAGGTCA CCTCTGAAGT GATTTTTTTT
18601 GAGTAAAAGG AAATCTTGAC TACTTTATAT TCTTAAAGGA ATATTCTTTA
18651 TATACTTCAA ATTTAGAACT TAACTTTAAA AGTTTTTCTT CTGTAATTGT
18701 TGAACGGGTG ATTATTATTA ACTCTAGATA AGCAGGTACT AGAAACCAAA
18751 ACTCAGAAAA TGTTTACTGT TAGAATTCTA TTAAATTTTA AGTGTTGTAT
18801 TCTTTTTCAT TGGGTGATGT CAGGGTGATA ACCAGACATT CATGGAAAGG
18851 CATGCAGTTT GTCCATTGTG ACAGTTTGTT TAATAAAACC ACATACACAC
18901 TTTATTTAAG ATTAAAATCT AACTGGAAAG TCAGCTTGGA AAATGGACAT
18951 TTCCAAGTAT GTTTGGTGAG TCACAGATAT AAAAATAGAA ATTCTGATGA
19001 GAGGTTTCAG TTTTTAATAC CAAGTCCTTA GGAGTCTTAA CATTGGCCAG
19051 CATCTGTTTA TCAAATGACA TAAATACGTA AACCTATAAG AATTAAGTTT
19101 ATTAATTAGG CAATTTATGT CTGTGATAAT TCTTACGGGA GAAAGAGGAT
19151 TTGATTGGAA AGCAGTTTGG GAAGAAAGTG CTGCTGAAAT TTCCAGAATT
19201 TAATTGATTG GTTACATAAA CTTTTTTGACT TCAGCGTTTG TTGTTGTTGT
19251 TCTTTTACTG TCCTTGTTTT CACATAAAAA CTATATGGAG CCAGGCACAG
19301 TGGCTCACGC CTGTAATCCC AGCATTTTGG GAGACCGAGG CAGGCGGATC
19351 ACCTGAGGCC AGGAGTTTGA GACCAGCCTT GCCAACATGG TGAAACCCTG
19401 TCTCTACTAA AGATACCAAA AAAGTGCTGG GTGTGGTGGC GGGCGCCTGT
```

FIGURE 3F

```
19451 AATCCCAGCT ACTCTGGAGG CTGAGGCATG AGAATTGCTT GAATCCAGGA
19501 GGCGGAGTTT GCAGTGAGCT GAGATTGTGC CACTGCACTC CAGCCTGGGC
19551 GACAGAGCGA GACTCCGTCT CAAAAAAAGA AAAAACAAAA CAAAACAAAA
19601 ACCCGGTATG TGGTAAATTA CTTAATTGGG CAAAAGAAAA AAATGTCTGT
19651 TGCTATGGTT CAGTCAGCCA GGTAGGAATA TTTTTTGTTG TAGAATTCCT
19701 AAGTGCTTAT TTCCAGATAC AGGTGAATTT TTGTTAAAAG TATCCCTGTT
19751 TCATAAGTGC ATTACACAAA TATTGGAGTT TTATCTGTTT AGGTTTTGTT
19801 TTTTTTTTAG ACTGAGTCTT GCTCTGTTGC CCAAGTTGGA GTGCAGTGGC
19851 GTGATCTCGG CTCACAGCAA CCTTCTTCCT CCTGGGTTCA AGCGATTCTC
19901 TTGACTCAGT TTCCCGAGTG GCTGGGATTA CAGGCATGTG CCACCAGGTC
19951 CTGCTAATTT TTGTATTTTT AGCAGAGGCA GGGTTTCACC ATGTTGTCGA
20001 GGCTGGTCTC AAACTCCTGA CCTCAAGTGA TCTTCCTGCC TCGGCCTCCC
20051 AAAGTGCTGG GATTAAAGGC ATGAGCCACT ATGCCTGGCT AATCTGTTTA
20101 TGTATTTTAA ACATAAAATG CATGGGATTT TCTTGTAGGA CAAATAATGA
20151 AACCAAGCTT GGTTTTCTAT GTTACTTAGG GGCAACATTT GTCAATACAG
20201 TAAGGCTGTG TTCCTAAAGT AGACTAGGAG TTTTTAAGAA AGCTGAAACA
20251 AAAAGTTTAT TGTAGAATGA CTGCATACAT TATGTTTAGG CCTCTGATAT
20301 AGTCCAAATA CAGTGACTTT ATTTCAGAAT AGTTGAACTG TATGTGATAA
20351 TTTTTTTAAA GAAGCATTTG ATGTTTAAAA ACAAGGTTTT TCCTGAGTTT
20401 ACCAGTGTAG CCCTACAGAT TAAGGTGTTT GCTATCCTTT ATTTTCCCCT
20451 TCATTTTATT TTTCCACTGC CATTGTACTA CCCAAGCCTC CTGTCCTTTC
20501 CCCCAATAAG TGCTTCAAGT TCCCAAATTA GTGTTTACTT TCTATGAAAA
20551 ACTCAGAGTA GCTGATCTCA GGATATAGGA GGAAAGAAAA ATATTCACAT
20601 TATTTCTTAC TAAGAAGTTA TTGATTGCTA ACCCCTGTC TCTTCTGAAA
20651 ATTTACGTTC TTCACAAAGG GTATTTGCTA ATTTCTAGGC CTAATTCATG
20701 GAATTTCGGG AATTAAAACG AAACTTTAAA AAATTAGGAT AGATGCAATG
20751 CTTAGAGGTT AGGGCAGTAC CTCTGGGATC ATTGAGTGTC TTTTGTCAAC
20801 CTTCCTTCCC CTCTTCTTTG AGCTTTCAAG TTCCTACTCT TAATTGCCTT
20851 TTTTCCTTGT ATTTCTGAAC TCATTTTGTC AAGTTCCAAG GTTTTTTTTT
20901 TTTTTTTTTT TTTTGACAGT GCCTTGAGCT TCAACACTAA AAGGGAAAAA
20951 GATTTAGAAT GGCCAATGCA CATGAATCCT TTGTAATTTA GGTATTTTTC
21001 TTAATAATTT GATACCTCAT AGAATTACTA TTTCTAGAAA TTCCATTGAA
21051 TTGTTTCTAG AAATTCCATT GAAGTCAAGC TTGATTTTTT TAGGAGGCAT
21101 TTGTAAAGTG CAGCTAAGTA GATTATTTCC AGCTTGCTGC TGCTGCTCAT
21151 TTTCTTGAGG TTTTTTTTCA TCCATGCATT CATGAAAATT TTCAGAGTAG
21201 TTGAATTCAA TTGACTCCTG CTGACAGCAA GGGG
(SEQ ID NO: 3)
```

FEATURES:

```
Start:    2007
Exon:     2007-2059
Intron:   2060-3118
Exon:     3119-3341
Intron:   3342-4462
Exon:     4463-4553
Intron:   4554-4948
Exon:     4949-5015
Intron:   5016-8054
Exon:     8055-8171
Intron:   8172-8258
Exon:     8259-8425
Intron:   8426-9007
Exon:     9008-9102
Intron:   9103-9352
Exon:     9353-9482
Intron:   9483-13437
Exon:     13438-13520
Intron:   13521-16514
Exon:     16515-16594
Intron:   16595-17962
Exon:     17963-18053
Intron:   18054-18139
Exon:     18140-18277
Stop:     18278
```

FIGURE 3G

SNPs:

| DNA Position | Major | Minor | Domain | Protein Position | Major | Minor |
|---|---|---|---|---|---|---|
| 76 | A | - | Beyond ORF(5') | | | |
| 7980 | C | T | Intron | | | |
| 8571 | C | T | Intron | | | |
| 11257 | T | C A | Intron | | | |
| 11684 | C | T | Intron | | | |
| 13312 | T | C | Intron | | | |
| 17110 | T | C | Intron | | | |
| 17451 | C | A | Intron | | | |
| 20766 | G | A | Beyond ORF(3') | | | |
| 20914 | T | - | Beyond ORF(3') | | | |

Context:

DNA Position

76
GCAGAAAAGTATAAAGATGGTAATCTCTGTAGGAAATTAGTCCCCATTATTTAGCTGTAA
AATTATAATTAAAAA
[A,-]
AAAAATCTTTGTTTCTAAATCTTTGCCACTGATTATTTCCTGAAAATACACTCCAGGAAG
AAGCATTTTTAAGTTAAAGCATGTGAACTCTTATTTCTTGCTACAGGTTCATATTTCTTT
TTCTAGAGAGTTTGCCAAATTATACAACGTGCTCCTTCATGCTCTCACCAATCTTGGCTG
TTTTGAAAGGCCAAGAATAATGTTTTGATTAAACTGAATTTTTAAATTTCTAACGAATTT
GTCCGCTGTCATATATTTATTGATCATTTGAACATCTTTTTATTCTTAGCCTATTTATTA

7980
TAATATCTGTGCATTGCCTGGCACAGAGTAGGCCTAGCCTGGTAAATGAATGAATGCTTT
CAACAGTAGCATATCCTATTTTTGGTTTACATTTGTATATATCTTTTAAAACTGTTGTTG
TATAAAATGTAATTAAATTTAAAATTCTAGGAGCAAACGTTAAAACTCATAAGTATTAAG
GGAATTATCACTTCATATAAAGTATTTTATCAAAATGTTTTAAGAAGATGTTATATGGAA
TCTGCTATAATATGTTCTGAAAGATTATTTTAAATGGCATAGAGGAATTGGTAATTAAGA
[C,T]
TATGCTTTAGAGCATAACATGGCTTCAGCTCACTCTTGTACATTTATCATTTTTATCTTA
ATTTTATTTTTAAGGGATGGCATGCATGTAGCAGTGAAAATCGTAAAAAATGTAGGCCGT
TACCGTGAAGCAGCTCGTTCAGAAATCCAAGTATTAGAGCACTTAAATAGTACTGATCCC
AATAGTGTCTTGTAAGTATAACTTTCACCTAGGAGCCATCATATTACATGAAATATTCAG
GTTTCCATAAACTGAATTATTATTTTGCTCTGTTTTAGCCGATGTGTCCAGATGCTAGAA

8571
GATGCTAGAATGGTTTGATCATCATGGTCATGTTTGTATTGTGTTTGAACTACTGGGACT
TAGTACTTACGATTTCATTAAAGAAAACAGCTTTCTGCCATTTCAAATTGACCACATCAG
GCAGATGGCGTATCAGATCTGCCAGTCAATAAATTGTAAGTACACTTGATAAATCTTTAT
TTTTATTTATTTATTTATTTATTTTGAGACGGAGTCTCGCTCTGTCACCCAGGCTG
GAGTGCAGTGGCGCTCTCGGGTCCCAGCAAGCTCAGCCTCCCGGGTTCACGCCATTTTCC
[C,T]
GCCTCAGCCTCCCGAGTAGCTGGGACTACAGGCGCCCACCACCATGCCCAGCTAATTTTT
TGTATTTTTAGTAGAGATGGGATTTCACAGTGTTAGCCAGGATGGTCTCGATCTCCTGAC
CTTGTGATTGCCCCCCTCGGCCTCCCAAAGTGCTGGGGTTATAGGCGTGAGCCACTGTGC
ACAGCAATAAATCTTTATTTTTAAATATTTTTTATGTTTGTACCTCCTTAACAATTAAGA
TAAATCTTTAAGCACCAGAAAACTTGTTTTTATTATACAAGCTATATATCCAAATGTTGT

11257
CACCACCACACCCGGCTAATTTTTATAGTTTTTAGTAGAGATGGGGTTTCACCATGTTAG
CCAGGCTGGTCTCGAACTCCTGACCTCAGGTGATCCTCCTGCCTCGGCCTCCCAAAGTGC
TTGGATTACAGGCGTGAGCCACCGCGCCCGGCCAAGGATTTTTTTTTTTTAATTTTTATG
TTTTTTATAACAGAGACAGGGCCTCACCATGTTGCACAGGCTGGTCTCGAACTCCTGGGC
TTAAGTGATCCGCCTGCCTTGGCCTCCCAAAGTGCTGGGATTATAGGTGTGAGCCACCGC
[T,C,A]
CCCACCAGAATATGGTCAATCTTATTAATAAAGTTCCAAATGTGGCCAAGCAAGGGATAG
TACAAATCTGAAATTGGAGTCCCTGGCCTTGAGGAGAAAGAATCAGGAGATTGGGAGAAT

FIGURE 3H

```
              AGAAAGGTCCTTTGTTTGTGGAGTGAGGATGAAGGCATAATGCAATTGGAGGGGAAAATG
              TAGTCAGGTGCTAGAGTTGAAGTAGGCAGTTGGCCTTATGTTGGGTATAAAAGCTAACTC
              ATCCAAGAATGAGATGATTTAGAATGGTGTACTGCAGAAGATTACAGTCACCTGGGAAAA

11684     GTCCTTTGTTTGTGGAGTGAGGATGAAGGCATAATGCAATTGGAGGGGAAAATGTAGTCA
              GGTGCTAGAGTTGAAGTAGGCAGTTGGCCTTATGTTGGGTATAAAAGCTAACTCATCCAA
              GAATGAGATGATTTAGAATGGTGTACTGCAGAAGATTACAGTCACCTGGGAAAAGACTAA
              ATTGGGAGATAGGAGTGGTTGAAAAATAAAACTTTTTTTTTTTTTTGAGACGCAGTCTTG
              CACTGTCACCCGGGCTGGACTGCAGTGGCACGATCTCGGCTCACTGCAACTTCTGCCTCC
              [C,T]
              GGGTTCAAGCGATTCTCCTGTGTCAGCCTCCCAAGTAGCTGGGCTTACAGGTGCCCGCCA
              CCACGCCCAGCTAATTTTTTGTATTTTTAGTAGAGATGGGGTTTCACCACATTGGCCAGG
              CTGGTCTCCAACTCCTGACCTTGTGATTCACCTGCCTTGGCCTCCCAAAGTGCTGGGATT
              ACAGGTGTGAGCCACCGTGCCTGGTTGAAAAATAAAACTTTTATGAGGTCCAAGCTCTAG
              CATTTACGGATTTTGTATGTGTTAATAGGTAGAAACCATGCTCCATTATTTATTTATTTA

13312     TAGTAATTTCATTCTGAGGATAATTATAAACCTGTATTTGTGCTAATAAAATATAAAAAT
              TCTTGGACTAACCATGAACTGAGCATAATAATGGTTTTAACAGCAGTGCTCTCCCATTAT
              ATAAACAGTTCAGAGACTATGGAATATTTGCACGAATTGGTTGTATACTTGGAAAATGGT
              AGCCCCCTTTTATTTTACATAACATGCACCCCTCCCTAGTTAGAATACTGTGTCTTGATG
              TGAGCATATGGACTATGGAGTGTGTTGAATAGCATTTGCTGTAAAACTAGAACTATAAAC
              [T,C]
              CTGAATTTGGTGTCTTATTCTCCCAAATGGGTTCTGTAAAGGGAGCACTCATATAGGGAA
              GGATTTAATGTACTGTCAATTAAAAGTTTTTGCATAGTAAAATGTTTCTATTTGTTTTAA
              AATAGCTTTAGGTTGGTCTCAGCCTTGTGATGTTTGGAGCATAGGTTGCATTCTTATTGA
              ATATTACCTTGGTTTCACAGTCTTTCAGGTACGTGGCTAGTAAATTCCATTTAATAATTC
              ATAACAAATTGTAAACGTTAAAGGTATGCTAAAGTTTTGACTTCCATATTGGAAAATTGC

17110     CACGATCTCAGCTCACTGCAGCCTCTGCCTCCTGGGTTCAAGTGATTCTTCTGCCTCAGC
              CCCCTGAGTCGCTGGGATTACAGGTGCCCACCACTATGCCTGGCTAATTTTTGTATTTTT
              AGTAGAGATGGGGTTTCACCGTGTTAGTCAGGCTGGTCTTGAACTCCTGACCTCAGGTGA
              TCTGCCTGCCTTGGCCTCCCAAAGTGCTGGAATTACAGGTGTGAGTCACTGCACTAGGCC
              ATGTTTTTAAAAACTAATATAATAAAAAATATTTACCTTGTGATCTAGTGCAGGGGTCCC
              [T,C]
              AACCCCTCGGAACTGGGCTGTACAACAGGAGGTGAGTGGCGGGTGAGTGAGCATTATTGC
              TGCCTGAGCTGCACCTCCTGTCAGATCAGCAGTGGCATTAGATTCTCATAGGAATGTGAA
              CCCTATTGTGAACTGCGCACGTGAGGGATCTACGTTGCATGAAGGTTCCTTATGAGAATC
              TAATGCCTGATGATCTGAGGTGGAAGTTTGATTCCAAACCATCATCCCTCCTCCCCGGAT
              CTGCTTCCATGAAACCGGTCCCTGGTTCCAAAAGGGTTGAGGACCACTGATCTAGTAAAC

17451     GGGTGAGTGAGCATTATTGCTGCCTGAGCTGCACCTCCTGTCAGATCAGCAGTGGCATTA
              GATTCTCATAGGAATGTGAACCCTATTGTGAACTGCGCACGTGAGGGATCTACGTTGCAT
              GAAGGTTCCTTATGAGAATCTAATGCCTGATGATCTGAGGTGGAAGTTTGATTCCAAACC
              ATCATCCCTCCTCCCCGGATCTGCTTCCATGAAACCGGTCCCTGGTTCCAAAAGGGTTGA
              GGACCACTGATCTAGTAAACAAAATGGCTTTTGGGTTTTTTTTGTTTTTTTTTTTTTTTT
              [C,A]
              ACTCAAGTTTACGTTTGGCATAAGTGTTTTCTTAGGCGATGTAAAAATAATACATAGAAT
              ATGGAAAAGCTTGTGTTTTGGAATCATATCACTCTAAGTGTGAAATTTATTCTGTCCTTA
              ACCAGCTGTATATTCTTAGACAAGGTGGTATTTCCAAACACAGCTTCATCGCAGAAGCCA
              CCGAGGGAGTTCTTTAAAGATTTCCAGCCCCATTCTAGATCTAGTGAAAACAGAATTTTA
              GGACTGGATCCAGGGGGCCCCTAGTTTTAAGCTGACATTGTTCCATATGTGATAGGAACA

20766     ACTGCCATTGTACTACCCAAGCCTCCTGTCCTTTCCCCCAATAAGTGCTTCAAGTTCCCA
              AATTAGTGTTTACTTTCTATGAAAAACTCAGAGTAGCTGATCTCAGGATATAGGAGGAAA
              GAAAAATATTCACATTATTTCTTACTAAGAAGTTATTGATTGCTAACCCCCTGTCTCTTC
              TGAAAATTTACGTTCTTCACAAAGGGTATTTGCTAATTTCTAGGCCTAATTCATGGAATT
              TCGGGAATTAAAACGAAACTTTAAAAAATTAGGATAGATGCAATGCTTAGAGGTTAGGGC
              [G,A]
              GTACCTCTGGGATCATTGAGTGTCTTTTGTCAACCTTCCTTCCCCTCTTCTTTGAGCTTT
              CAAGTTCCTACTCTTAATTGCCTTTTTTCCTTGTATTTCTGAACTCATTTTGTCAAGTTC
              CAAGGTTTTTTTTTTTTTTTTTTTTTTGACAGTGCCTTGAGCTTCAACACTAAAAGGGA
              AAAAGATTTAGAATGGCCAATGCACATGAATCCTTTGTAATTTAGGTATTTTTCTTAATA
              ATTTGATACCTCATAGAATTACTATTTCTAGAAATTCCATTGAATTGTTTCTAGAAATTC

20914     GAAGTTATTGATTGCTAACCCCCTGTCTCTTCTGAAAATTTACGTTCTTCACAAAGGGTA
```

FIGURE 3I

```
TTTGCTAATTTCTAGGCCTAATTCATGGAATTTCGGGAATTAAAACGAAACTTTAAAAAA
TTAGGATAGATGCAATGCTTAGAGGTTAGGGCAGTACCTCTGGGATCATTGAGTGTCTTT
TGTCAACCTTCCTTCCCCTCTTCTTTGAGCTTTCAAGTTCCTACTCTTAATTGCCTTTTT
TCCTTGTATTTCTGAACTCATTTTGTCAAGTTCCAAGGTTTTTTTTTTTTTTTTTTTTT
[T,-]
GACAGTGCCTTGAGCTTCAACACTAAAAGGGAAAAAGATTTAGAATGGCCAATGCACATG
AATCCTTTGTAATTTAGGTATTTTTCTTAATAATTTGATACCTCATAGAATTACTATTTC
TAGAAATTCCATTGAATTGTTTCTAGAAATTCCATTGAAGTCAAGCTTGATTTTTTTAGG
AGGCATTTGTAAAGTGCAGCTAAGTAGATTATTTCCAGCTTGCTGCTGCTGCTCATTTTC
TTGAGGTTTTTTTTCATCCATGCATTCATGAAAATTTTCAGAGTAGTTGAATTCAATTGA
```

Chromosome map:

Chromosome 5

FIGURE 3J

ISOLATED HUMAN KINASE PROTEINS, NUCLEIC ACID MOLECULES ENCODING HUMAN KINASE PROTEINS, AND USES THEREOF

RELATED APPLICATIONS

The present application a divisional of U.S. application Ser. No. 09/810,671, filed Mar. 19, 2001 now U.S. Pat. No. 6,455,291, issued Sep. 24, 2002, which claims priority to U.S. Provisional Application No. 60/227,470, filed Aug. 24, 2000.

FIELD OF THE INVENTION

The present invention is in the field of kinase proteins that are related to the serine-arginine-rich protein kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books,* Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine,* McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) *Annu. Rev. Cell. Biol.* 8:463–93). Regulation of PTK activity may therefore be an important strategy in controlling some types of cancer.

The phosphorylation of proteins on serine/threonine and/or tyrosine residues is now well established as a principal mechanism in the control of many cellular functions, such as the cell cycle, differentiation and signal transduction. Serine/threonine protein kinases add phosphate moiety to a serine or threonine residue of the substrate. Protein kinase substrates include elements of signal transduction pathway such as transcription factors or ion channels, as well as structural proteins such as filaments and cellular motors. Family of protein kinases is one of the largest in the genome. Classification of kinases is based on their sequence, tissue localization and domain topology.

Primary structures of kinases are rather conserved; functional prediction based on the sequence alone is difficult. A number of soluble and transmembrane proteins contain kinase domains along with other structural components; these multi-domain proteins are often referred to as kinases. Because of this additional information, multi-domain kinases are easier to classify. Tissue specific expression of kinases is often defined by transcription regulatory elements.

Serine- and arginine-rich (SR) proteins were originally characterized by a shared epitope that cross-reacts with the monoclonal antibody mAb104, at least one N-terminal RNA recognition motif and a basic C-terminal domain rich in serine and arginine residues, often arranged in tandem repeats. Since that time, many more potential SR proteins or SR-like proteins have been identified using different monoclonal antibodies, so that the number of such proteins may well reach 80 or more. There is evidence that the SR domain is involved in protein—protein interactions as well as protein-RNA interactions, and may serve as a localization signal directing proteins to nuclear speckles The kinase of the present invention is similar to Serine- and arginine-rich (SR) or CDC like kinase 4, which is involved in cell cycle control. CDC like kinase 4 is one of the serine-arginine-rich (SR) protein kinases. The substrates of these enzymes include the components of splicing machinery. By changing their substrates' phosphorylation states, they affect these proteins' activities and intracellular distribution. As a result of modification, their substrates may select different splice sites, which results in alternative splice variants. CLK and SRPK are the two notable examples of SR kinases. CLK is involved in regulation of splicing, like most of SR kinases, while SRPK phosphorylates protamine, a small basic arginine-rich protein that replaces histamine in developing spermatozoa. Unlike other SR kinases, SRPK is localized in cytoplasm and expressed predominantly in germ cells.

The human CDC like kinase 4 gene of the present invention can be expressed in yeast to identify possible interactors; this can be done by means of a complementation assay or a two-hybrid experiment. Artificially synthesized enzyme as well as derived peptides can be used to activate or inhibit cellular processes modulated by this kinase. Immunoassay or PCR may be used to measure the concentration of this protein and detect abnormally developing tissue or cancerous growth.

For a review of serine-arginine-rich (SR) protein kinases and CDC like kinase 4, see the references of Nayler et al. Biochem J Sep. 15, 1997 326 (Pt 3):693–700, Colwill et al., EMBO J Jan. 15, 1996 15(2):265–75, Papoutsopoulou et al., Nucleic Acids Res Jul. 15, 1999 27(14):2972–80.

Kinase proteins, particularly members of the serine-arginine-rich protein kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the serine-arginine-rich protein kinase subfamily.

SUMMARY OF THE INVENTION

The present invention is based in part on the identification of amino acid sequences of human kinase peptides and proteins that are related to the serine-arginine-rich protein kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte.

DESCRIPTION OF THE FIGURE SHEETS

FIGS. 1A–1B provide the nucleotide sequence of a cDNA molecule or transcript sequence that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte.

FIGS. 2A–2D provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIGS. 3A–3D provide genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs, including insertion/deletion variants ("indels"), were identified at 10 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the serine-arginine-rich protein kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the serine-arginine-rich protein kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the serine-arginine-rich protein kinase subfamily and the expression pattern observed. Experimental data as provided in FIG. 1 indicates expression in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known serine-arginine-rich protein family or subfamily of kinase proteins.

Specific Embodiments
Peptide Molecules

The present invention provides nucleic acid sequences that encode protein molecules that have been identified as being members of the kinase family of proteins and are related to the serine-arginine-rich protein kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et a. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated by the data presented in FIG. 3, the map position was determined to be on chromosome 5 by ePCR.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. As indicated by the data presented in FIG. 3, the map position was determined to be on chromosome 5 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in the gene encoding the transporter protein of the present invention. SNPs were identified at 10 different nucleotide positions in introns and regions 5' and 3' of the ORF. Such SNPs in introns and outside the ORF may affect control/regulatory elements.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte by a virtual northern blot. In addition, PCR-based tissue screening panel indicates expression in leukocyte. A large percentage of pharmaceutical agents are being developed that modulate the activity of kinase proteins, particularly members of the serine-arginine-rich protein subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte. Such uses can readily be determined using the information provided herein, that which is known in the art, and routine experimentation.

The proteins of the present invention (including variants and fragments that may have been disclosed prior to the present invention) are useful for biological assays related to kinases that are related to members of the serine-arginine-rich protein subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis,myeloid cell as well as leukocyte by a virtual northern blot. In addition, PCR-based tissue screening panel indicates expression in leukocyte.

The protein of the present invention is similar to CDC like kinase 4, which is involved in cell cycle control. CDC like kinase 4 is one of the so-called serine-arginine-rich (SR) protein kinases. The substrates of these enzymes include the components of splicing machinery. By changing their substrates' phosphorylation states, they affect these proteins' activities and intracellular distribution. As a result of modification, their substrates may select different splice sites, which results in alternative splice variants. CLK and SRPK are the two notable examples of SR kinases. CLK is involved in regulation of splicing, like most of SR kinases, while SRPK phosphorylates protamine, a small basic arginine-rich protein that replaces histamine in developing spermatozoa. Unlike other SR kinases, SRPK is localized in cytoplasm and expressed predominantly in germ cells.

The human CDC like kinase 4 gene of the present invention can be expressed in yeast to identify possible interactors; this can be done by means of a complementation assay or a two-hybrid experiment. Artificially synthesized enzyme as well as derived peptides can be used to activate or inhibit cellular processes modulated by this kinase. Immunoassay or PCR may be used to measure the concentration of this protein and detect abnormally developing tissue or cancerous growth.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte by a virtual northern blot. In addition, PCR-based tissue screening panel indicates expression in leukocyte.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte by a virtual northern blot. In addition, PCR-based tissue screening panel indicates expression in leukocyte. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 5 by ePCR.

FIG. 3 provides information on SNPs that have been found in the gene encoding the transporter protein of the present invention. SNPs were identified at 10 different nucleotide positions in introns and regions 5' and 3' of the ORF. Such SNPs in introns and outside the ORF may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs, including insertion/deletion variants ("indels"), were identified at 10 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 5 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte by a virtual northern blot. In addition, PCR-based tissue screening panel indicates expression in leukocyte. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte by a virtual northern blot. In addition, PCR-based tissue screening panel indicates expression in leukocyte.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte by a virtual northern blot. In addition, PCR-based tissue screening panel indicates expression in leukocyte. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the transporter protein of the present invention. SNPs were identified at 10 different nucleotide positions in introns and regions 5' and 3' of the ORF. Such SNPs in introns and outside the ORF may affect control/regulatory elements. As indicated by the data presented in FIG. 3, the map position was determined to be on chromosome 5 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286–295 (1992)), electrophoretic mobility of mutant and wild type nucleic acid is compared (Orita et al., PNAS 86:2766 (1989); Cotton et al., Mutat. Res. 285:125–144 (1993); and Hayashi et al., Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the transporter protein of the present invention. SNPs were identified at 10 different nucleotide positions in introns and regions 5' and 3' of the ORF. Such SNPs in introns and outside the ORF may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in the bone osteosarcoma cell line, breast, uterus leiomyosarcoma, fetal heart, infant brain, colon-juvenile granulose tumor, colon-moderately differentiatd adenocarcinoma, bone marrow hematopoietic stem cells, pooled human melanocyte, fetal heart, and pregnant uterus, normal nerve, leukopheresis, myeloid cell as well as leukocyte by a virtual northern blot. In addition, PCR-based tissue screening panel indicates expression in leukocyte. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the transporter protein of the present invention. SNPs were identified at 10 different nucleotide positions in introns and regions 5' and 3' of the ORF. Such SNPs in introns and outside the ORF may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV inmediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual 2nd, ed., Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide having an amino acid sequence consisting of SEQ ID NO:2.

2. An isolated CDC-like kinase having an amino acid sequence comprising SEQ ID NO:2.

3. A composition comprising the polypeptide of claim 1 and a carrier.

4. A composition comprising the CDC-like kinase of claim 2 and a carrier.

5. An isolated polypeptide consisting of an amino acid sequence having at least 99% sequence identity to SEQ ID NO:2.

6. An isolated CDC-like kinase comprising an amino acid sequence having at least 99% sequence identity to SEQ ID NO:2.

7. A composition comprising the polypeptide of claim 5 and a carrier.

8. A composition comprising the CDC-like kinase of claim 6 and a carrier.

* * * * *

SEQUENCE LISTING

<160> NUMBER OF SEQ ID NOS: 5

<210> SEQ ID NO 1
<211> LENGTH: 2354
<212> TYPE: DNA
<213> ORGANISM: Homo sapien

<400> SEQUENCE: 1

| | | | | | |
|---|---|---|---|---|---|
| gccagctggg | gttactttaa | aaaacatgct | ccatgtgcat | ccctcttgaa | gcttcgcact | 60 |
| ctgttgaaga | ggacactcat | cccagtcatt | atttagaagc | aaggtccttg | aatgagcgag | 120 |
| attatcggga | ccggagatac | gttgacgaat | acaggaatga | ctactgtgaa | ggatatgttc | 180 |
| ctagacatta | tcacagagac | attgaaagcg | ggtatcgaat | ccactgcagt | aaatcttcag | 240 |
| tccgcagcag | gagaagcagt | cctaaaagga | agcgcaatag | acactgttca | agtcatcagt | 300 |

| | | | |
|---|---|---|---|
| cacgttcgaa | gagccaccga | aggaaaagat | ccaggagtat | agaggatgat | gaggagggtc | 360 |
| acctgatctg | tcaaagtgga | gacgttctaa | gagcaagata | tgaaatcgtg | acactttgg | 420 |
| gtgaaggagc | ctttggcaaa | gttgtagagt | gcattgatca | tggcatggat | ggcatgcatg | 480 |
| tagcagtgaa | aatcgtaaaa | aatgtaggcc | gttaccgtga | agcagctcgt | tcagaaatcc | 540 |
| aagtattaga | gcacttaaat | agtactgatc | ccaatagtgt | cttccgatgt | gtccagatgc | 600 |
| tagaatggtt | tgatcatcat | ggtcatgttt | gtattgtgtt | tgaactactg | ggacttagta | 660 |
| cttacgattt | cattaaagaa | aacagctttc | tgccatttca | aattgaccac | atcaggcaga | 720 |
| tggcgtatca | gatctgccag | tcaataaatt | ttttacatca | taataaatta | acccatacag | 780 |
| atctgaagcc | tgaaaatatt | tgtttgtga | agtctgacta | tgtagtcaaa | tataattcta | 840 |
| aaatgaaacg | tgatgaacgc | acactgaaaa | acacagatat | caaagttgtt | gactttggaa | 900 |
| gtgcaacgta | tgatgatgaa | catcacagta | ctttggtgtc | tacccggcac | tacagagctc | 960 |
| ccgaggtcat | tttggcttta | ggttggtctc | agccttgtga | tgtttggagc | ataggttgca | 1020 |
| ttcttattga | atattacctt | ggtttcacag | tctttcagac | tcatgatagt | aaagagcacc | 1080 |
| tggcaatgat | ggaacgaata | ttaggaccca | taccacaaca | catgattcag | aaaacaagaa | 1140 |
| aacgcaagta | ttttcaccat | aaccagctag | attgggatga | acacagttct | gctggtagat | 1200 |
| atgttaggag | acgctgcaaa | ccgttgaagg | aatttatgct | ttgtcatgat | gaagaacatg | 1260 |
| agaaactgtt | tgacctggtt | cgaagaatgt | tagaatatga | tccaactcaa | agaattacct | 1320 |
| tggatgaagc | attgcagcat | cctttctttg | acttattaaa | aagaaatga | aatgggaatc | 1380 |
| agtggtctta | ctatatactt | ctctagaaga | gattacttaa | gactgtgtca | gtcaactaaa | 1440 |
| cattctaata | tttttgtaaa | cattaaatta | tttgtacag | ttaagtgtaa | atattgtatg | 1500 |
| ttttgtatca | atagcataat | taacttgtta | agcaagtatg | gtcttgataa | tgcattagaa | 1560 |
| aaattaaaat | taattttct | ttttgaaatt | accatttta | aataccttg | aaatatcctt | 1620 |
| tgtgtccagt | gataaatgtg | attgatcttg | cctttgtac | atggaggtca | cctctgaagt | 1680 |
| gattttttt | gagtaaaagg | aaatcttgac | tactttatat | tcttaaagga | atattcttta | 1740 |
| tatacttcaa | atttagaact | taactttaaa | agtttttctt | ctgtaattgt | tgaacgggtg | 1800 |
| attattatta | actctagata | agcaggtact | agaaaccaaa | actcagaaaa | tgtttactgt | 1860 |
| tagaattcta | ttaaatttta | agtgttgtat | tcttttcat | tgggtgatgt | cagggtgata | 1920 |
| accagacatt | catggaaagg | catgcagttt | gtccattgtg | acagtttgtt | taataaaacc | 1980 |
| acatacacac | tttatttaag | attaaaatct | aactggaaag | tcagcttgga | aaatggacat | 2040 |
| ttccaagtat | gtttggtgag | tcacagatat | aaaaatagaa | attctgatga | gaggtttcag | 2100 |
| ttttttaatac | caagtcctta | ggagtcttaa | cattggccag | catctgttta | tcaaatgaca | 2160 |
| taaatacgta | aacctataag | aattaagttt | attaattagg | caatttatgt | ctgtgataat | 2220 |
| tcttacggga | gaaagaggat | ttgattggaa | agcagtttgg | gaagaaagtg | ctgctgaaat | 2280 |
| ttccagaatt | taattgattg | gttacataaa | cttttgact | tcagaaaaaa | aaataaaaa | 2340 |
| aacaaaaaaa | aaac | | | | | 2354 |

<210> SEQ ID NO 2
<211> LENGTH: 445
<212> TYPE: PRT
<213> ORGANISM: Homo sapien

<400> SEQUENCE: 2

Met Cys Ile Pro Leu Glu Ala Ser His Ser Val Glu Glu Asp Thr His

-continued

```
  1               5              10              15
Pro Ser His Tyr Leu Glu Ala Arg Ser Leu Asn Glu Arg Asp Tyr Arg
             20                  25              30

Asp Arg Arg Tyr Val Asp Glu Tyr Arg Asn Asp Tyr Cys Glu Gly Tyr
         35                  40              45

Val Pro Arg His Tyr His Arg Asp Ile Glu Ser Gly Tyr Arg Ile His
     50                  55              60

Cys Ser Lys Ser Ser Val Arg Ser Arg Ser Ser Pro Lys Arg Lys
 65              70                  75                  80

Arg Asn Arg His Cys Ser Ser His Gln Ser Arg Ser Lys Ser His Arg
                 85              90              95

Arg Lys Arg Ser Arg Ser Ile Glu Asp Asp Glu Glu Gly His Leu Ile
             100             105             110

Cys Gln Ser Gly Asp Val Leu Arg Ala Arg Tyr Glu Ile Val Asp Thr
             115             120             125

Leu Gly Glu Gly Ala Phe Gly Lys Val Val Glu Cys Ile Asp His Gly
     130             135             140

Met Asp Gly Met His Val Ala Val Lys Ile Val Lys Asn Val Gly Arg
145             150             155                     160

Tyr Arg Glu Ala Ala Arg Ser Glu Ile Gln Val Leu Glu His Leu Asn
                 165             170             175

Ser Thr Asp Pro Asn Ser Val Phe Arg Cys Val Gln Met Leu Glu Trp
             180             185             190

Phe Asp His His Gly His Val Cys Ile Val Phe Glu Leu Leu Gly Leu
             195             200             205

Ser Thr Tyr Asp Phe Ile Lys Glu Asn Ser Phe Leu Pro Phe Gln Ile
     210             215             220

Asp His Ile Arg Gln Met Ala Tyr Gln Ile Cys Gln Ser Ile Asn Phe
225             230             235             240

Leu His His Asn Lys Leu Thr His Thr Asp Leu Lys Pro Glu Asn Ile
             245             250             255

Leu Phe Val Lys Ser Asp Tyr Val Lys Tyr Asn Ser Lys Met Lys
             260             265             270

Arg Asp Glu Arg Thr Leu Lys Asn Thr Asp Ile Lys Val Val Asp Phe
             275             280             285

Gly Ser Ala Thr Tyr Asp Asp Glu His His Ser Thr Leu Val Ser Thr
     290             295             300

Arg His Tyr Arg Ala Pro Glu Val Ile Leu Ala Leu Gly Trp Ser Gln
305             310             315             320

Pro Cys Asp Val Trp Ser Ile Gly Cys Ile Leu Ile Glu Tyr Tyr Leu
             325             330             335

Gly Phe Thr Val Phe Gln Thr His Asp Ser Lys Glu His Leu Ala Met
             340             345             350

Met Glu Arg Ile Leu Gly Pro Ile Pro Gln His Met Ile Gln Lys Thr
             355             360             365

Arg Lys Arg Lys Tyr Phe His Asn Gln Leu Asp Trp Asp Glu His
             370             375             380

Ser Ser Ala Gly Arg Tyr Val Arg Arg Cys Lys Pro Leu Lys Glu
385             390             395             400

Phe Met Leu Cys His Asp Glu His Glu Lys Leu Phe Asp Leu Val
                 405             410             415

Arg Arg Met Leu Glu Tyr Asp Pro Thr Gln Arg Ile Thr Leu Asp Glu
             420             425             430
```

Ala Leu Gln His Pro Phe Phe Asp Leu Leu Lys Lys Lys
    435                 440             445

<210> SEQ ID NO 3
<211> LENGTH: 21234
<212> TYPE: DNA
<213> ORGANISM: Homo sapien

<400> SEQUENCE: 3

| | | | | | |
|---|---|---|---|---|---|
| gcagaaaagt | ataaagatgg | taatctctgt | aggaaattag | tccccattat | ttagctgtaa | 60 |
| aattataatt | aaaaaaaaaa | atctttgttt | ctaaatcttt | gccactgatt | atttcctgaa | 120 |
| aatacactcc | aggaagaagc | atttttaagt | taaagcatgt | gaactcttat | ttcttgctac | 180 |
| aggttcatat | ttctttttct | agagagtttg | ccaaattata | caacgtgctc | cttcatgctc | 240 |
| tcaccaatct | tggctgtttt | gaaaggccaa | gaataatgtt | ttgattaaac | tgaattttta | 300 |
| aatttctaac | gaatttgtcc | gctgtcatat | atttattgat | catttgaaca | tctttttatt | 360 |
| cttagcctat | ttattaaagt | attttttattg | atttagaaga | gcttttttatt | acaaatatttt | 420 |
| aaccatttgt | catatatata | ttgcatagtg | tcttttcttt | atgatttgtc | ttttggaggt | 480 |
| agcctgtgaa | ttggtctccc | tttctacagg | cttagttaat | ccattctgca | ttagaaagac | 540 |
| tgatgtggct | gtaaacccta | cctttatata | ttgtggtcag | aagcctgtaa | cataaagtat | 600 |
| caagtcttaa | accagtgatt | ctccaacttt | agtgtgaata | agaatcacct | tggaggtatg | 660 |
| ctgaccagat | ttacagtcag | tgagtatgac | ctaaggccca | gggttaccat | ttttaataag | 720 |
| aactccatat | ttgatactgt | tgataaatag | accgtccttt | gagaaataat | actctttagc | 780 |
| ctagcacgca | gggtttttaa | tgatgctatt | ctcagcttac | ttatttgtct | acattcccct | 840 |
| atgtgaaaat | tgctcttgct | gggattgtct | ttttcctgag | taatgcatag | acaattccat | 900 |
| ctctaagcca | ttgtggctaa | aagtgccata | tgaatttaag | atggtaatat | gccattcttc | 960 |
| tcccccggaa | tttcttctgt | attctacttt | tccaaatcc | tggcttccct | ttaagatgca | 1020 |
| actctatttc | catcttttttt | gtaattattc | tctgaccatt | ttaaacagat | ttttccccc | 1080 |
| atctctgact | ctaagcactc | atgtgttgta | accttttaga | atttcctaca | ttgttggatt | 1140 |
| ttgtttcatt | tttatgtgag | taatctcaaa | ttgttcatta | tttgttggca | gggacttttgc | 1200 |
| cttatataat | ttttttttta | tctcccacag | gacctgtgtg | gatataaaaa | cgaatgccct | 1260 |
| taccctcatc | cgtcttggct | atttgaaagg | ctatagtgaa | atattcactg | ggcattcagt | 1320 |
| ggataattta | aaaaattaaa | tcagtctgtt | catcctgtcc | atagcctgtg | taattctgta | 1380 |
| gactttgttt | atataatctc | tcagccttgg | tcattggcca | ttatctattg | aagagactct | 1440 |
| catccttttta | gtttgtcctc | atggtgttca | ctcccatgtt | ttgttactct | atacgttgtt | 1500 |
| tatggcttag | cagctctaat | tccatgcagt | attccagcta | aagattgtta | gtgctagttt | 1560 |
| tttctaatag | aaggattttg | gacttttatg | ggaaggatgc | ccttaagagt | atggtcacgt | 1620 |
| ctagcttatt | gtattggtga | tctctccctg | acagttccaa | gccaactgat | cagatctcta | 1680 |
| acctagacta | cccacagtct | tacccaaata | tcctgagttg | tttctccaat | aaaatacaac | 1740 |
| ttaaagctga | tgctagggaa | agagaaccgg | gtttctgtat | ctccccagcc | tggatttgat | 1800 |
| gctagcccta | ttgggtagta | gttgtaaaga | tgcttctatt | tctgcctaaa | ccagcccct | 1860 |
| gggaaaaaga | atgacagcat | attctgggga | aaggaaaggg | gttggtgagg | gcaatctagt | 1920 |
| caacatccgt | cactccattg | cttgttaggc | ttatttttagc | cgatgtgtct | gactgggcag | 1980 |
| gtgtcccctc | tctccctcag | tgctccatgt | gcatccctct | tgaagcttcg | cactctgttg | 2040 |

-continued

```
aagaggacac tcatcccagg tagagagggg gacgggaaac tgggccaatt gaatctatgt    2100
cctttctttt ccatcagatc aaggccactt aactgggatc cattgacatc ctgaggccca    2160
tgacctttga aattccttgc caagttttgt ttatgtgttt cttaggaaag agagtccatg    2220
gctttcagca gattttcaaa gggatctcta gattaaagca cgatggcact agatgatggt    2280
gttttctgtt gtttcttagg tatttctcaa acaggaatga caggaaatta gaaatgcaaa    2340
gggaagtagg gtggtggaac tattgtaatg ctaaactaca ggatcccttt cttattttag    2400
ggggatatat tttagatgcc tttggcacat gaggcagtcc tcaaaagcta tgttttctat    2460
ttctcaaaca ggaataacaa ggctagaaat gcaaagagta gaggagacat gatagatgct    2520
gtgtgtaata aaattggcct gtataatagt ggtttgaaaa tattttagtt tttgtcacta    2580
atgttgttat acaaccttgg taaatcattt ttcttctagg gatcttaatg tagtcgtcgg    2640
taaaatgaaa gggctggaat acatttaagg ctccttatag ctctaatata cctttcatga    2700
aggaattctc tctgtgccag ggatatctaa aatgctctta cattacaaga gaaggaatc    2760 cttttttgcct gcctctgatt gtacctctgt gagagactaa gacagcttag atacaggtgc    2820
agaaggtaaa ggaacactta atcaagtaaa cactagacat gaattaatga tttgactcaa    2880
gctttattcc ttggtgtgaa gtgcttgaca gcaaactcta taatgggccc atttgcttgt    2940
ttgttaaagt aaaattattt cttaagcttt atgagataaa tataaatgct aattcatctg    3000
tttgaatttt tttcttatat tgagttagct gtttaagaat ttctgagaaa atgttttgtt    3060
tgaaccacat tattgcagaa tgaagagaat aatttgaaat cttttaatgt gtttgcagtc    3120
attatttaga agcaaggtcc ttgaatgagc gagattatcg ggaccggaga tacgttgacg    3180
aatacaggaa tgactactgt gaaggatatg ttcctagaca ttatcacaga gacattgaaa    3240
gcgggtatcg aatccactgc agtaaatctt cagtccgcag caggagaagc agtcctaaaa    3300
ggaagcgcaa tagacactgt tcaagtcatc agtcacgttc ggtatgattg gttttgtttt    3360
caatttgagt ggagttttat ttgtgtgtac tcttaacgag ctgataagtt tctaatttt    3420 tatatatata tatataaaat actatttgga tatattataa ttgtatttat attacttaaa    3480
tccttaaagg aaacctccaa attcttgtag ctgatctgta tatttattag ctagccctca    3540
tttgcccaca tttcctcata ttctgcagac cagataatga gtttattgat tttaataata    3600
aaactatttt tttatttgta acatattctt atgaaaaat catgcaccca tatcttttct    3660
ttcatcttaa gcattttttt tttcttagaa accctttatc tggtacttga aaataaatgt    3720
gaaatattgc actggtggac acctgaatgt tactaacctg catagagcat agttccatag    3780
tccagtgcat cattgtctgc aatgaattct tttgaagttg tgaaaatggg tgctgaatgg    3840
gaaacatcca aaagtctgc ccccccttt ttttttttaa cactcagaca tcttcacctg    3900
cttgaacagt gaactttgaa ttagtttctc cccaagtttt cttcagtaaa actagttttt    3960
attagattga acattgaaat taactagcct ttattttccc cttttatttt aatcatgtat    4020 atttaaaat attgctaaat tagaataatt tcaaatagtc ttgacatttt aaaacatttt    4080
tctgaaaaac tagacatctc aattcacagc atatgctgtt tatagcaaga gataagtaaa    4140
tcatgacatt gcattcttta aatttcagac ttcaattaaa tcagtatttt aaagagacaa    4200
ttgtgttgtt ttttctatt gccactttaa gtatcttatc tgaaaatctg ttccttgcca    4260 tgttttttctt ctgtaacata aactgtgccc tgtgaatttc tggggactga atttgaaatt    4320
gctcctgcca actgttcgtg gcctggtgct tatctgaatg cctgaatatc tccccgctga    4380
```

-continued

```
atgaattgcg tattctgccc tgaattcact ctgatatatt gattggctgg acgatcttgg    4440
tgctgcccac ttgccgttcc agaagagcca ccgaaggaaa agatccagga gtatagagga    4500
tgatgaggag ggtcacctga tctgtcaaag tggagacgtt ctaagagcaa gatgtataga    4560
atattttca acactttta aactttgcag aaagaataat cttttaaga atagtttgtc       4620
agcgggggc taaagaactc ttcattgctt ttttatttg ctttttgtgg gtttgtttgt      4680
tcttttatat ttcttctttt ctgtagaatt taaatatttc tattctaaag ttccaaaata    4740
atcagtggaa tttgagatta gagcaagaaa gatagctcta tctaattgtt tttgtagcag    4800
ctgaaactaa ataatttga gtgctgaaac cttagttatg ctttgttaga gatcatttga    4860
aaatattcca cacttaagca ttcattgttt gaagaactag acagtttgta ctcaggtact    4920
tacacctctt tttccctcct cactctagat gaaatcgtgg acactttggg tgaaggagcc    4980
tttggcaaag ttgtagagtg cattgatcat ggcatgtaag tttgttttt ccttttcaaa     5040
cattctgatg ttttggtgg ggaaagattc ataattcaga tgaaatttta tttatttatt    5100
tatttgagat agggcctctg ttgcccaggc ttgagtgcag tggtgctatc ttggctcact    5160
gcaactgccg cctcccggct tcaagtgatt ctcctgcttc agcctctcaa gtagctggga    5220
ttacaggagc ctgccaccac acctagctag ttttgtatt tttaatagag atggggtttc     5280
accgtgttgg cctgggtggt ctcgaactcc tgacctcaag tgatctaccc gcctcagttt    5340
cccaaaacgt tgggattaca agcctgagcc cctgtgcccg gccaagatgg aatatatttt    5400
aaatggtagc cacgtgtttt gggggtaaa ttactcacca aagtttcttg aactttgtat    5460
gatttattta ccgtgaatgt ggatcttaag aatgctgact gccgggcaca gtggctcact    5520
cctgtaatcg cagcactttg ggaggccaag gcaggtggat cacctgaggt tgggagttca    5580
agactagcct gaccaacatg gagaaataca ttctctacta aaaatacaaa attagccagg    5640
tgtggtggca catgcctgta atcccagttg cttgggaggc tgaggcagga gaatcacttg    5700
aacccaggag gggaggaagg cggaggttgc ggtgagccaa gattgtgcca ttgcactcca    5760
gcctaggcaa cgagtgaaaa tccgtctcaa aaaaataaa aataaaaaaa agaatgatg     5820
acaaatttca acaggggaa atcattgaaa ttaaagtgga tgttcaagtg aaggaatttc    5880
ccagaactcc agaactgagg cccttgaccc tgtatataag atttggcaat ttcggattac    5940
agaggcaata aagcatgtct aatcttaaat gttaagagtt agcttcctaa actataaaga    6000
catttattta tctagggcct agagaataaa gtttgtgatt tgacccttc tgcctcattt     6060
taccgttttc ctctaggacc tctattttgt ggcttgaaaa cttttgtaag agaagctctt    6120
agaacttttg cgaaacttca catttctaaa atgacaaaat tttttatcat aaattatttg    6180
ggaaggatgt aatttccaac ctgttgtaaa tattaatatt aaaaaataaa acttacctct    6240
ctctaaatgc atttcaggga atctaaatac catagcagct tgatacctac catcatccat    6300
aaacaaactc ttcttgaata cttagaaatg ttttattatt gaatttattg tcatttcact    6360
ttccataaat actatcctaa attatcccca catttttgctt ttctgcaaca aatatgtgaa   6420
tgtaaattga actttaaagt attttgaaat attttcagac ttacagaaaa attgataaaa    6480
tagttcaaag aattcccata tattccaaat gttaacctat tttccaaatg tttacatttt    6540
ataagatttg ctttatcatt atacatacat ttgtttcaa attttgccaa ctaatctgca    6600
gactttattc agatttcacc agtcatccca ttaatgtcct tttagaattt cttgaaagtc   6660
taagtcttgg tgtatttaat gaaatgtatc ttaaaacaaa ttttttttta atgagatgga    6720
gtctcactgt gttgctctgg ctggtgtgga actcctggcc tcaagtgatc cttctgcctc    6780
```

```
agcctcccat agtgctggga ttacaggtgt gagccctgt agtcacgtgt ggcacacacc   6840
tgtaccacat ctggcctgga atgttttctt tattggggca gttgaggcct ctaaaaaatg   6900
agtacatata gccatagata aatatctgac tgtctagcat tgtatgtttt cttttttcat   6960
tttcgtggat acaagcactg agaaaacttt ttggtcatat aattaaatag ataggagtag   7020
aagctttgtc acagtaatct tattagagtt cttttaagtc ttgaggtata tgccaagcat   7080 taaaaattt ttttagtgac ttatcagttc acattcgttg gggccttgtt gaaagcaatg   7140
aactggaaac cactggatgt ggaaaaggt tttgtatcca gccattagaa tacgtgtttg   7200
tttgccccaa atgtttttat agcctagggc atacatcctg ttacactagt aagagatggg   7260
tatggttttg taaagtggaa gggtcatagt gaaaagaag gcttgaatgc tggctcatct   7320
gtaggtagat taggtttaaa aaggaagaca aaaataaatt gaagatttgc aacatttatg   7380
gctctatact ttttaggaag cattcttaca gatgccgcag tctaaagccc actgccctcc   7440
cctgtagctg tttctgtata ctggcatcag tgcatctgct aaggttttc tgggcttcat   7500 tacttagagt tggggtctcc tttacctgga tgtttccttc ccaatctgac aaactcccag   7560
ctatctttca ggactcagtt ctgtgtcacc tcttctgtga agaagtctaa gttgtttctg   7620
tgtctgtctt ttccattaga ctttgaagta cgtagggaca cacccgtct tttaatcact   7680 aatatctgtg cattgcctgg cacagagtag gcctagcctg gtaaatgaat gaatgctttc   7740
aacagtagca tatcctattt tggtttaca tttgtatata tcttttaaaa ctgttgttgt   7800
ataaaatgta attaaattta aaattctagg agcaaacgtt aaaactcata agtattaagg   7860
gaattatcac ttcatataaa gtattttatc aaaatgtttt aagaagatgt tatatggaat   7920
ctgctataat atgttctgaa agattatttt aaatggcata gaggaattgg taattaagat   7980
tatgctttag agcataacat ggcttcagct cactcttgta catttatcat ttttatctta   8040
atttattttt taagggatgg catgcatgta gcagtgaaaa tcgtaaaaaa tgtaggccgt   8100
taccgtgaag cagctcgttc agaaatccaa gtattagagc acttaaatag tactgatccc   8160
aatagtgtct tgtaagtata actttcacct aggagccatc atattacatg aaatattcag   8220
gtttccataa actgaattat tattttgctc tgttttagcc gatgtgtcca gatgctagaa   8280
tggtttgatc atcatggtca tgtttgtatt gtgtttgaac tactgggact tagtacttac   8340
gatttcatta aagaaaacag ctttctgcca tttcaaattg accacatcag gcagatggcg   8400
tatcagatct gccagtcaat aaattgtaag tacacttgat aaatctttat ttttatttat   8460
ttatttattt atttattttg agacggagtc tcgctctgtc acccaggctg gagtgcagtg   8520
gcgctctcgg gtcccagcaa gctcagcctc ccgggttcac gccattttcc cgcctcagcc   8580
tcccgagtag ctgggactac aggcgcccac caccatgccc agctaatttt ttgtattttt   8640
agtagagatg ggatttcaca gtgttagcca ggatggtctc gatctcctga ccttgtgatt   8700 gccccctcg gcctcccaaa gtgctgggt tataggcgtg agccactgtg cacagcaata   8760
aatctttatt tttaaatatt tttatgtttt gtacctcctt aacaattaag ataaatcttt   8820
aagcaccaga aaacttgttt ttattataca agctatatat ccaaatgttg tcactaaaaa   8880
aacagacatt ttacaagtaa agatgaatcg tctcttgacc actatatcct ttgccagtcc   8940
tcctttccct cctagtacaa attaagtttg taagtgaaac taataatgtg cttttgttct   9000
cttgtagttt tacatcataa taaattaacc catacagatc tgaagcctga aaatatttg   9060 tttgtgaagt ctgactatgt agtcaaatat aattctaaaa tggtaagtta aagacttgtt   9120
```

-continued

```
ttaatttggg tggttgtctt taaaattaat ttaacttgat gatctttgga tgaggaattt      9180
cacttctgag ccttattata tcctgttgtt taaccaaaaa gaagtaatcc ttctttgcct      9240
ttctcatgag cttactttga caatcaagaa gataattcat gtgctggcct tttgagtagc      9300
gctataaaat gtatctattg agtttcatgt ttactcaact gtgtctctct agaaacgtga      9360
tgaacgcaca ctgaaaaaca cagatatcaa agttgttgac tttggaagtg caacgtatga      9420
tgatgaacat cacagtactt tggtgtctac ccggcactac agagctcccg aggtcatttt      9480
gggtcagtag acaccaggct ttctaatatt ataattgaag aagagatttt tgttctttac      9540
agctttactg gtggggtggg aagtatgat cttctcagca ggattcagaa aacgttttct       9600
attttcataa aaatgtgtg gacattgcta taaatacttt tcctgagtgg taaacatgtg       9660
atactgtctg ggaaagatat tccaggtggt ggttattttt gaacaagtaa atcttaaatg      9720
atcataagag aacaggctgt gttagctaaa tgcatcaaag aaatgtgatt ttgaagttat      9780
atgagtacct attttcatgc catcacaaaa gcacatggct ggtaaaaata ctgaggaaac      9840
tggttggcag atgtctagaa tataggatgg ataaaggtca agagaagaaa gaggcttctc     9900
taagagctcc tgtgataacc cttgatgtga gaaagtctgg gaaagaaaat gagttaaggt      9960
gcagagtttt caaataagaa gggacttatt aagggagtgt tatgcctcaa cattaaaagt     10020
tatagatcag gtgtgttaat aaatcaggga agtcagagat tggcttggga gcttggagac     10080
attgggaaac attcagatca ggcatatcaa gagagttgaa tgtaataagc tgattactta     10140
gcctaaagtt aggtccaact gaggttagat tgtaaagcat ttttgtggaa tcgtatttta     10200
atacttttta cttttttgt gtgtccaacg ggacttggta gttcagaata ggagtgtaaa      10260
agcaaactct tgatacttac ctagagtaga gtagtaaagg agtgaggaaa tcaagaatcc     10320
tgtgcagctc ttgcccacag aacttcccct tgatgacaga atgttccatt tctgcactgt     10380
cccatatggt agccactagt cactgtgcgt gactgactac cttgtagtgg ggccagtgtg     10440
actgaggaga actgagtttt gaatttacat taatttttatt tcagatttaa acagccacat    10500
gtggctagtg gttaccatat tgaacaagca caactcttag agcttgtctt ttaaatgcgt     10560
aataataggg tttctgcgta gtacaaattg aaaggagcta ctgtgtaagg gtaaaagaaa     10620
gcaatatggg aagagatagt ggacagagag gtattttcag agattagaag gcaatagatt     10680
cctcatttta agaatcagat ttttcccccaa atatttggca tttttttcttt gttattggta   10740
tatcaaacag tggtgcatcg tacagtgtgc tatcctagat tgagtaaaat atagtatata    10800
gtaaccccc ccttttttt ttctttgaga tggagtttca ctttgtcacc caggctggag      10860
tgcagtggta ccatctcggc tcactgcaac ctccacctcc caggttcgcg cgattctcct     10920
aactcagcct cctgagtagc tgggattaca ggtgcccacc accacacccg ctaattttt     10980
atagttttta gtagagatgg ggtttcacca tgttagccag gctggtctcg aactcctgac     11040
ctcaggtgat cctcctgcct cggcctccca aagtgcttgg attacaggcg tgagccaccg     11100
cgccggcca aggatttttt tttttaatt tttatgtttt ttataacaga gacagggcct       11160
caccatgttg cacaggctgg tctcgaactc ctgggcttaa gtgatccgcc tgccttggcc     11220
tcccaaagtg ctgggattat aggtgtgagc caccgcaccc accagaatat ggtcaatctt     11280
attaataaag ttccaaatgt ggccaagcaa gggatagtac aaatctgaaa ttggagtccc     11340
tggccttgag gagaaagaat caggagattg ggagaataga aagtcccttt gtttgtggag     11400
tgaggatgaa ggcataatgc aattggaggg gaaaatgtag tcaggtgcta gagttgaagt     11460
aggcagttgg ccttatgttg ggtataaaag ctaactcatc caagaatgag atgatttaga     11520
```

```
atggtgtact gcagaagatt acagtcacct gggaaaagac taaattggga gataggagtg   11580
gttgaaaaat aaaactttt tttttttttg agacgcagtc ttgcactgtc acccgggctg   11640
gactgcagtg gcacgatctc ggctcactgc aacttctgcc tcctgggttc aagcgattct   11700
cctgtgtcag cctcccaagt agctgggctt acaggtgccc gccaccacgc ccagctaatt   11760
ttttgtattt tagtagaga tggggtttca ccacattggc caggctggtc tccaactcct   11820
gaccttgtga ttcacctgcc ttggcctccc aaagtgctgg gattacaggt gtgagccacc   11880
gtgcctggtt gaaaataaa acttttatga ggtccaagct ctagcattta cggattttgt   11940
atgtgttaat aggtagaaac catgctccat tatttattta tttatttttt gagacagagt   12000
ctcactctgt tgcctggcct ggagtgcagt ggtgcaatct cagctcactg caacctctgc   12060
ctcccgggtt caagcgattc tcctgcctca gcctcctgag tagctgggat tacaagtgca   12120
caccaccaca cccaactaat ttatatatat atatatatat atattttaaa attttattt   12180 tttatttttg ttatttgttt atttatttt ttgagatgga gttttgcttt tattgcccag   12240
gctagagtgc agtggcgcaa tctcagctta ctgcaacctc tgccttccgg tttcaagcca   12300
ttctcctgcc tcagcctccc aagtcactgg gattacaggc gtctgccacc acgcccagct   12360 aattttttg tattttagt agagacgggg tttcaccatg ttggtcagac tggtctcgaa   12420
ctgccaacct ggtgatccac ccgcctcggc ctcccaaagt gctgggatta caggcatgag   12480
ccaccgcgcc tgcccatgc tctattatta tccatttgtt caaatgacag acactggagc   12540
ggatggttaa caaaaatgac ttaagtcatt atatattgac ttgaatatat ttcttctttt   12600
atctttaact tcagtgataa tgaaagtaat tgaaatgtct ttgaatgtag attttattta   12660 tacattttt aactaaatat ttgatctttg aaatattaaa atatctatgt ggttggttct   12720
ttctccttcc cagtcagtat agatttaaga aggctagatg ttttattctg atctgaataa   12780
tactgtcatt gagaattctg aaggagaaag tatataaaat catgtataga cagcgccgat   12840
gtttatgtat agatccctct ctgagctcca atgtgtctgt aatttctgct tataggtgaa   12900
actgcttaaa attcccatta tacctttat acaatttgtg caaaacggta atatttctct   12960
taacggaaga agtaaactca tgcatcaagc tgatgataat tgataaggca ttagtaattt   13020
cattctgagg ataattataa acctgtattt gtgctaataa aatataaaaa ttcttggact   13080
aaccatgaac tgagcataat aatggtttta acagcagtgc tctcccatta tataaacagt   13140
tcagagacta tggaatattt gcacgaattg gttgtatact tggaaaatgg tagcccccctt   13200 ttatttaca taacatgcac ccctcctag ttagaatact gtgtcttgat gtgagcatat   13260
ggactatgga gtgtgttgaa tagcatttgc tgtaaaacta gaactataaa ctctgaattt   13320
ggtgtcttat tctcccaaat gggttctgta aagggagcac tcatataggg aaggatttaa   13380
tgtactgtca attaaaagtt tttgcatagt aaaatgtttc tatttgtttt aaaatagctt   13440
taggttggtc tcagccttgt gatgtttgga gcataggttg cattcttatt gaatattacc   13500
ttggtttcac agtctttcag gtacgtggct agtaaattcc atttaataat tcataacaaa   13560
ttgtaaacgt taaaggtatg ctaaagttt gacttccata ttggaaaatt gccatacatc   13620
attattcttg agattaaaac ttaggcaaaa tggtcattct ttaaaaccac agttgaatga   13680
aatattacta tgagtgagtg atcatagtta attttgcatg tgattagtgt tgtaacaca   13740 tggttcatat atggttcata ctgtctcctt ttttaaattg tagagcttct tcataaattt   13800
gcagtagtgt taatgtggcc agttttcagt tatagttatg ttgactatca atatggccat   13860
```

-continued

```
gaacgagtca cttattcctt tttataaaag aattcaggaa caacaaggga ttgtatttta   13920
ctcttaagta ttaagcatct ataatgtctt aggcatttct aagtataagt acataaaggt   13980
gaagagacaa catctttctc aagtcatgca aaagacattg gaaagttatc gcagtatagt   14040
gtagcatttg ctgtgatgga acaacgtaga aagtgtaggt agggagggcc aggcggggta   14100
gctcacacct gtaatcccag cactttggga ggctgaggtg ggtggatcat gaggtcagga   14160
gatcgagacc atcctggcta acatggtgaa accctgtctc tactaaaagt ataaaaatt    14220
agctgggcgt ggtggcgggc gcctgtagtc ccagctactc gggaggctga ggcaggagaa   14280
tggcgtgaac ctgggaggcg gagcttgcag tgagcgagat catgccactg cactccagcc   14340
tggacaacag ggtgagactc tgttgcaaaa aaaaaaaaa aaaaaaaag acaaagtgta     14400
ggtagggaga acccaggaaa ggttaataat tactttagag aaggcgtcac tgagaacata   14460
ggaagaggag gaggagttag aaaactggag tgcaatgggc atataaggaa gaagaaatag   14520
tatctgtaaa tgcacagagg agtaaaggaa catattctac tcagggaaga atagcgttgt   14580
cagagtgtct tgtataaatg ggaaaattat aacaataggc aaggatcaat tcataaaaga   14640
cttcgcaagg tattggtttg atcctagaag tcagtggatt ccaaaagtag actggtccaa   14700
aatgaaaatg gttgtctagg tttgccattc tgacccttat ttagagatta tccctcctgc   14760
ttttttttt tttaatgtct cttttatgta atgatagtca tagttgttgg tagtttgctt    14820
ttaaaaataa aaagtcctta attggtaaaa caaaaagtag gaaactctac tttcttttcc   14880
actctgtcct taagttgtac ttacatctga aatcttaatt tttttttttt tttccctgag   14940
atggagtctc actgtgtcac ccaggctgga gtgcagtggc gcaacgtcag ctcactgcaa   15000
cctctgcctc ccgggttcaa gtgattctca tgtctcagcc tcccaagtag ctgggattac   15060
aggcacgagc cactcaccc cactaatttt ttgtattttt agtagagggt tttgctgtgt     15120
tgaccaggct ggtctcgaac tcctgacctc aagtgatcta ccctccttgg cctcccaaag   15180
tgctgggatt acaggtgtga gccaccgcac ccagcctgaa atttaaattc ttgaaagctt   15240
taggtgatgc aaccattgaa gaactttaaa tagggtcatg gtatgatcga ggtgttgtgt   15300
tgttttgttt ggggaagagg ggctggagat cccagctagt actgttgagg ttgatttgaa   15360
gttagagcag tgcaggggc atgcagctat gatgggctaa gagtcactta ggcagctgtt    15420
gcacaatgat gaattccctg ttcgtggggc acctcgccag atttctgttt ctgtctaatc   15480
tgtagagatc ctgttgaaaa gtactctgag tttatagata agtttgatgt cttagaatca   15540
tggttattaa tcagttctgg gaggtattgt ctggttttgc agtggtgagc tgtagggtca   15600
agaaaaagtt aagcaaagtg aatgctttca tcaatctgac taatatgaaa tggatgcttc   15660
cggtgatttt gtgattataa atcactttga gttttaaatg aagtatatat tatttgagag   15720
gtggtttata ttttaactcc accctgcaaa atactcttaa actaaggaat ttctttaaaa   15780
tgtgaagcta gtattactta ttcctgtcat gtatcacaac gatttggaag caatatgcaa   15840
ggcacagtag ttgatagatt tcttttaaaa gtgttgcata cagcctctgc tctccagaac   15900
aagggttagc aaactttggc ccatggtgaa atcctgcctg gtgcctgttt ttacaaaaag   15960
aagaagagta tgcaataggg accactcatg acgagccaag cctaaaatat ttactatctg   16020
gcccttttaca gaagtttgcc aacctctgct ctagaagcat accattccag ctgtaagttt   16080
gaccgttttc tgtattctac ttcagccaag cctccgttac taatttaagg atatgtgctt   16140
tgacatgggt tgatagctta actttcctca tatatgagct atatgacttt gaggtagtat   16200
cttaaccttt ttgaaattca tgttcccaca tacctagctc agaattgttt agagaattat   16260
```

```
tgggactgta tgtatgtctg ttgcctggga gtagtaagtg ttaacaagtg aactattcat    16320
tgggtactgg atgttaattt tggttaagca gctgattaaa tgaggagaca gttttctctgg   16380 taaccttgcc cagttattct ttaaacagtg taagaagtgc aaataaagaa ggaaactaaa    16440
attttagatt aaacaagtta atgtgtttgt agggaaatgg agagtactaa atttcttttt    16500
cttacatgtt ttagactcat gatagtaaag agcacctggc aatgatggaa cgaatattag    16560
gacccatacc acaacacatg attcagaaaa caaggtatgt tttaagattc aagactttttg   16620 ttggatatgt gcaatagcat atattcaaac tacagaaaac ccaacgttgt tgtaatactg    16680
attccaagga ctatagattt tgacttttttt ttttttttct gtactggagg taacttctaa   16740
cttcatctta ctccttttttt ttttttgag atggagtctc actctgtcac ccaggctgga   16800
gtgcagtggc acgatctcag ctcactgcag cctctgcctc ctgggttcaa gtgattcttc    16860
tgcctcagcc ccctgagtcg ctgggattac aggtgcccac cactatgcct ggctaattttt   16920 tgtatttttta gtagagatgg ggtttcaccg tgttagtcag gctggtcttg aactcctgac   16980
ctcaggtgat ctgcctgcct tggcctccca aagtgctgga attacaggtg tgagtcactg    17040
cactaggcca tgttttttaaa aactaatata ataaaaaata tttaccttgt gatctagtgc   17100
aggggtcccc aaccctcgg  aactgggctg tacaacagga ggtgagtggc gggtgagtga    17160
gcattattgc tgcctgagct gcacctcctg tcagatcagc agtggcatta gattctcata   17220
ggaatgtgaa ccctattgtg aactgcgcac gtgagggatc tacgttgcat gaaggttcct   17280
tatgagaatc taatgcctga tgatctgagg tggaagtttg attccaaacc atcatccctc    17340
ctccccggat ctgcttccat gaaaccggtc cctggttcca aaagggttga ggaccactga    17400
tctagtaaac aaaatggctt ttgggttttt tttgttttttt ttttttttttt aactcaagtt    17460 tacgtttggc ataagtgttt tcttaggcga tgtaaaaata atacatagaa tatgagaaag    17520
cttgtgtttt ggaatcatat cactctaagt gtgaaattta ttctgtcctt aaccagctgt    17580
atattcttag acaaggtggt atttccaaac acagcttcat cgcagaagcc accgagggag    17640
ttctttaaag atttccagcc ccattctaga tctagtgaaa acagaatttt aggactggat    17700
ccagggggcc cctagtttta agctgacatt gttccatatg tgataggaac aacttagttg    17760
agagactaaa acctcacagg gtggaggata tgaggtgtcc gatatataat tgttgctgag    17820 gttttttaaaa attgtatgca tctatattat ataagtctat acacttagag agagctgctt   17880
tccatgtctc ccctcatggg tgcagggtaa agatacgact cttgttattt tactaatcca    17940 gactttttttt ttttttctgt agaaaacgca agtattttca ccataaccag ctagattggg    18000
atgaacacag ttctgctggt agatatgtta ggagacgctg caaaccgttg aaggtaaaag    18060
aaaaaagatt aaaggttaaa taaaccacgt gtttgcacta ttaataattt tttttaaaac    18120
aaaaacattt ctcccccagg aatttatgct ttgtcatgat gaagaacatg agaaactgtt    18180
tgacctggtt cgaagaatgt tagaatatga tccaactcaa agaattacct tggatgaagc    18240
attgcagcat ccttttctttg acttattaaa aaagaaatga aatgggaatc agtggtctta    18300
ctatatactt ctctagaaga gattacttaa gactgtgtca gtcaactaaa cattctaata    18360 ttttttgtaaa cattaaatta ttttgtacag ttaagtgtaa atattgtatg ttttgtatca    18420
atagcataat taacttgtta agcaagtatg gtcttgataa tgcattagaa aaattaaaat    18480 taattttttct ttttgaaatt accatttttta aatacctttg aaatatcctt tgtgtccagt    18540
gataaatgtg attgatcttg ccttttgtac atggaggtca cctctgaagt gatttttttt    18600
```

-continued

```
gagtaaaagg aaatcttgac tactttatat tcttaaagga atattcttta tatacttcaa    18660
atttagaact taactttaaa agttttctt ctgtaattgt tgaacgggtg attattatta    18720
actctagata agcaggtact agaaaccaaa actcagaaaa tgtttactgt tagaattcta    18780 ttaaattta agtgttgtat tcttttcat tgggtgatgt cagggtgata accagacatt    18840
catggaaagg catgcagttt gtccattgtg acagtttgtt taataaaacc acatacacac    18900
tttatttaag attaaaatct aactggaaag tcagcttgga aaatggacat ttccaagtat    18960
gtttggtgag tcacagatat aaaaatagaa attctgatga gaggtttcag ttttaatac    19020 caagtcctta ggagtcttaa cattggccag catctgttta tcaaatgaca taaatacgta    19080
aacctataag aattaagttt attaattagg caatttatgt ctgtgataat tcttacggga    19140
gaaagaggat ttgattggaa agcagtttgg gaagaaagtg ctgctgaaat tccagaatt    19200 taattgattg gttacataaa ctttttgact tcagcgtttg ttgttgttgt tcttttactg    19260
tccttgtttt cacataaaaa ctatatggag ccaggcacag tggctcacgc ctgtaatccc    19320 agcatttgg gagaccgagg caggcggatc acctgaggcc aggagtttga ccagccttt    19380 gccaacatgg tgaaaccctg tctctactaa agataccaaa aaagtgctgg gtgtggtggc    19440
gggcgcctgt aatcccagct actctggagg ctgaggcatg agaattgctt gaatccagga    19500
ggcggagttt gcagtgagct gagattgtgc cactgcactc cagcctgggc gacagagcga    19560
gactccgtct caaaaaaga aaaacaaaa caaaacaaaa acccggtatg tggtaaatta    19620
cttaattggg caaaagaaaa aaatgtctgt tgctatggtt cagtcagcca ggtaggaata    19680 tttttttgttg tagaattcct aagtgcttat ttccagatac aggtgaattt ttgttaaaag    19740
tatccctgtt tcataagtgc attacacaaa tattggagtt ttatctgttt aggttttgtt    19800 tttttttag actgagtctt gctctgttgc ccaagttgga gtgcagtggc gtgatctcgg    19860
ctcacagcaa ccttcttcct cctgggttca agcgattctc ttgactcagt ttcccgagtg    19920
gctgggatta caggcatgtg ccaccaggtc ctgctaattt ttgtattttt agcagaggca    19980
gggtttcacc atgttgtcga ggctggtctc aaactcctga cctcaagtga tcttcctgcc    20040
tcggcctccc aaagtgctgg gattaaaggc atgagccact atgcctggct aatctgttta    20100
tgtattttaa acataaaatg catgggattt tcttgtagga caaataatga aaccaagctt    20160
ggttttctat gttacttagg ggcaacattt gtcaatacag taaggctgtg ttcctaaagt    20220
agactaggag ttttttaagaa agctgaaaca aaaagtttat tgtagaatga ctgcatacat    20280
tatgtttagg cctctgatat agtccaaata cagtgacttt atttcagaat agttgaactg    20340
tatgtgataa ttttttttaaa gaagcatttg atgtttaaaa acaaggtttt tcctgagttt    20400
accagtgtag ccctacagat taaggtgttt gctatccttt attttcccct tcattttatt    20460
tttccactgc cattgtacta cccaagcctc ctgtcctttc ccccaataag tgcttcaagt    20520
tcccaaatta gtgtttactt tctatgaaaa actcagagta gctgatctca ggatatagga    20580
ggaaagaaaa atattcacat tatttcttac taagaagtta ttgattgcta accccctgtc    20640
tcttctgaaa atttacgttc ttcacaaagg gtatttgcta atttctaggc ctaattcatg    20700
gaatttcggg aattaaaacg aaactttaaa aaattaggat agatgcaatg cttagaggtt    20760
agggcagtac ctctgggatc attgagtgtc ttttgtcaac cttccttccc ctcttctttg    20820
agctttcaag ttcctactct taattgcctt ttttccttgt atttctgaac tcattttgtc    20880
aagttccaag gtttttttt tttttttttt ttttgacagt gccttgagct tcaacactaa    20940
aagggaaaaa gatttagaat ggccaatgca catgaatcct ttgtaattta ggtatttttc    21000
```

-continued

```
ttaataattt gatacctcat agaattacta tttctagaaa ttccattgaa ttgtttctag    21060
aaattccatt gaagtcaagc ttgattttt taggaggcat ttgtaaagtg cagctaagta    21120
gattatttcc agcttgctgc tgctgctcat tttcttgagg ttttttttca tccatgcatt    21180
catgaaaatt ttcagagtag ttgaattcaa ttgactcctg ctgacagcaa gggg         21234
```

<210> SEQ ID NO 4
<211> LENGTH: 427
<212> TYPE: PRT
<213> ORGANISM: Homo sapien

<400> SEQUENCE: 4

```
His Tyr Leu Glu Ala Arg Ser Leu Asn Glu Arg Asp Tyr Arg Asp Arg
  1               5                  10                  15

Arg Tyr Val Asp Glu Tyr Arg Asn Asp Tyr Cys Glu Gly Tyr Val Pro
             20                  25                  30

Arg His Tyr His Arg Asp Ile Glu Ser Gly Tyr Arg Ile His Cys Ser
         35                  40                  45

Lys Ser Ser Val Arg Ser Arg Ser Ser Pro Lys Arg Lys Arg Asn
 50                  55                  60

Arg His Cys Ser Ser His Gln Ser Arg Ser Lys Ser His Arg Arg Lys
 65                  70                  75                  80

Arg Ser Arg Ser Ile Glu Asp Asp Glu Glu Gly His Leu Ile Cys Gln
             85                  90                  95

Ser Gly Asp Val Leu Arg Ala Arg Tyr Glu Ile Val Asp Thr Leu Gly
            100                 105                 110

Glu Gly Ala Phe Gly Lys Val Val Glu Cys Ile Asp His Gly Met Asp
        115                 120                 125

Gly Met His Val Ala Val Lys Ile Val Lys Asn Val Gly Arg Tyr Arg
130                 135                 140

Glu Ala Ala Arg Ser Glu Ile Gln Val Leu Glu His Leu Asn Ser Thr
145                 150                 155                 160

Asp Pro Asn Ser Val Phe Arg Cys Val Gln Met Leu Glu Trp Phe Asp
                165                 170                 175

His His Gly His Val Cys Ile Val Phe Glu Leu Leu Gly Leu Ser Thr
            180                 185                 190

Tyr Asp Phe Ile Lys Glu Asn Ser Phe Leu Pro Phe Gln Ile Asp His
        195                 200                 205

Ile Arg Gln Met Ala Tyr Gln Ile Cys Gln Ser Ile Asn Phe Leu His
210                 215                 220

His Asn Lys Leu Thr His Thr Asp Leu Lys Pro Glu Asn Ile Leu Phe
225                 230                 235                 240

Val Lys Ser Asp Tyr Val Val Lys Tyr Asn Ser Lys Met Lys Arg Asp
                245                 250                 255

Glu Arg Thr Leu Lys Asn Thr Asp Ile Lys Val Val Asp Phe Gly Ser
            260                 265                 270

Ala Thr Tyr Asp Asp Glu His His Ser Thr Leu Val Ser Thr Arg His
        275                 280                 285

Tyr Arg Ala Pro Glu Val Ile Leu Ala Leu Gly Trp Ser Gln Pro Cys
290                 295                 300

Asp Val Trp Ser Ile Gly Cys Ile Leu Ile Glu Tyr Tyr Leu Gly Phe
305                 310                 315                 320

Thr Val Phe Gln Thr His Asp Ser Lys Glu His Leu Ala Met Met Glu
                325                 330                 335
```

Arg Ile Leu Gly Pro Ile Pro Gln His Met Ile Gln Lys Thr Arg Lys
            340                 345                 350

Arg Lys Tyr Phe His His Asn Gln Leu Asp Trp Asp Glu His Ser Ser
            355                 360                 365

Ala Gly Arg Tyr Val Arg Arg Cys Lys Pro Leu Lys Glu Phe Met
            370                 375                 380

Leu Cys His Asp Glu Glu His Glu Lys Leu Phe Asp Leu Val Arg Arg
385                 390                 395                 400

Met Leu Glu Tyr Asp Pro Thr Gln Arg Ile Thr Leu Asp Glu Ala Leu
            405                 410                 415

Gln His Pro Phe Phe Asp Leu Leu Lys Lys Lys
            420                 425

<210> SEQ ID NO 5
<211> LENGTH: 429
<212> TYPE: PRT
<213> ORGANISM: Homo sapien

<400> SEQUENCE: 5

Ser His Tyr Leu Glu Ser Arg Ser Ile Asn Glu Lys Asp Tyr His Ser
1               5                   10                  15

Arg Arg Tyr Ile Asp Glu Tyr Arg Asn Asp Tyr Thr Gln Gly Cys Glu
            20                  25                  30

Pro Gly His Arg Gln Arg Asp His Glu Ser Arg Tyr Gln Asn His Ser
            35                  40                  45

Ser Lys Ser Ser Gly Arg Ser Gly Arg Ser Ser Tyr Lys Ser Lys His
            50                  55                  60

Arg Ile His His Ser Thr Ser His Arg Arg Ser His Gly Lys Ser His
65                  70                  75                  80

Arg Arg Lys Arg Thr Arg Ser Val Glu Asp Asp Glu Glu Gly His Leu
            85                  90                  95

Ile Cys Gln Ser Gly Asp Val Leu Ser Ala Arg Tyr Glu Ile Val Asp
            100                 105                 110

Thr Leu Gly Glu Gly Ala Phe Gly Lys Val Val Glu Cys Ile Asp His
            115                 120                 125

Lys Ala Gly Gly Arg His Val Ala Val Lys Ile Val Lys Asn Val Asp
            130                 135                 140

Arg Tyr Cys Glu Ala Ala Arg Ser Glu Ile Gln Val Leu Glu His Leu
145                 150                 155                 160

Asn Thr Thr Asp Pro Asn Ser Thr Phe Arg Cys Val Gln Met Leu Glu
            165                 170                 175

Trp Phe Glu His His Gly His Ile Cys Ile Val Phe Glu Leu Leu Gly
            180                 185                 190

Leu Ser Thr Tyr Asp Phe Ile Lys Glu Asn Gly Phe Leu Pro Phe Arg
            195                 200                 205

Leu Asp His Ile Arg Lys Met Ala Tyr Gln Ile Cys Lys Ser Val Asn
            210                 215                 220

Phe Leu His Ser Asn Lys Leu Thr His Thr Asp Leu Lys Pro Glu Asn
225                 230                 235                 240

Ile Leu Phe Val Gln Ser Asp Tyr Thr Glu Ala Tyr Asn Pro Lys Ile
            245                 250                 255

Lys Arg Asp Glu Arg Thr Leu Ile Asn Pro Asp Ile Lys Val Val Asp
            260                 265                 270

Phe Gly Ser Ala Thr Tyr Asp Asp Glu His His Ser Thr Leu Val Ser

-continued

```
                275                 280                 285
Thr Arg His Tyr Arg Ala Pro Glu Val Ile Leu Ala Leu Gly Trp Ser
    290                 295                 300

Gln Pro Cys Asp Val Trp Ser Ile Gly Cys Ile Leu Ile Glu Tyr Tyr
305                 310                 315                 320

Leu Gly Phe Thr Val Phe Pro Thr His Asp Ser Lys Glu His Leu Ala
                325                 330                 335

Met Met Glu Arg Ile Leu Gly Pro Leu Pro Lys His Met Ile Gln Lys
            340                 345                 350

Thr Arg Lys Arg Lys Tyr Phe His His Asp Arg Leu Asp Trp Asp Glu
        355                 360                 365

His Ser Ser Ala Gly Arg Tyr Val Ser Arg Ala Cys Lys Pro Leu Lys
    370                 375                 380

Glu Phe Met Leu Ser Gln Asp Val Glu His Glu Arg Leu Phe Asp Leu
385                 390                 395                 400

Ile Gln Lys Met Leu Glu Tyr Asp Pro Ala Lys Arg Ile Thr Leu Arg
                405                 410                 415

Glu Ala Leu Lys His Pro Phe Phe Asp Leu Leu Lys Lys
            420                 425
```